US008377640B2

(12) United States Patent
Nagy

(10) Patent No.: US 8,377,640 B2
(45) Date of Patent: Feb. 19, 2013

(54) DIAGNOSTIC SCREENS FOR ALZHEIMER'S DISEASE

(75) Inventor: Zsuzsanna Nagy, Birmingham (GB)

(73) Assignee: ISIS Innovation Ltd., Oxford (GB)

( * ) Notice: Subject to any disclaimer, the term of this patent is extended or adjusted under 35 U.S.C. 154(b) by 71 days.

(21) Appl. No.: 12/870,987

(22) Filed: Aug. 30, 2010

(65) Prior Publication Data

US 2011/0045483 A1    Feb. 24, 2011

Related U.S. Application Data

(63) Continuation-in-part of application No. 10/659,578, filed on Sep. 10, 2003, now abandoned, which is a continuation of application No. PCT/GB02/01137, filed on Dec. 3, 2002.

(30) Foreign Application Priority Data

Dec. 3, 2001    (GB) .................................. 0106051.6

(51) Int. Cl.
*C12Q 1/68*    (2006.01)
(52) U.S. Cl. .......................................... 435/6.1; 435/29
(58) Field of Classification Search ........................ None
See application file for complete search history.

(56) References Cited

U.S. PATENT DOCUMENTS

2011/0045483 A1* 2/2011 Nagy ................................. 435/6
2012/0115152 A1* 5/2012 Nagy ........................... 435/6.11

OTHER PUBLICATIONS

Arendt T, Holzer M and Gartner U, "Neuronal expression of cycline dependent kinase inhibitors of the INK4 family in Alzheimer's disease," *J Neural Transm*, 105:949-960 (1998).
Arendt T, Rodel L, Gartner U, and Holzer M, "Expression of the cyclin-dependent kinase inhibitor p16 in Alzheimer's disease," *NeuroReport*, 7:3047-3049 (1996).
Burke WJ, McLaughlin JR, Chung HD, Gillespie KN, Grossberg GT, Luque FA, and Zimmerman J, "Occurrence of Cancer in Alzheimer and Elderly Control Patients: An Epidemiologic Necropsy Study," *Alzheimer Disease and Associated Disorders*, vol. 8:No. 1, pp. 22-28 (1994).
Darzynkiewicz Z, "Mammalian cell-cycle analysis," *The Cell Cycle—A Practical Approach*, Fantes P and Brooks R (eds), Oxford University Press, Oxford, pp. 43-68 (1993).
Davies KJ, "The Broad Spectrum of Responses to Oxidants in Proliferating Cells: A New Paradigm for Oxidative Stress," *IUBMB Life*, 48:41-47 (1999).
Drabkin HA and Erickson P, "Down Syndrome and Leukemia, An Update," *Etiology and Pathogenesis of Down Syndrome*, pp. 169-176 (1995).
Eckert A, Hartmann H, Forst H, and Muller WE, "Alterations of Intracellular Calcium Regulation During Aging and Alzheimer's Disease in Nonneuronal Cells," *Life Sciences*, vol. 55, Nos. 25/26, pp. 2019-2029 (1994).

Fischman HK, Reisberg B, Albu P, Ferris SH, and Rainer JD, "Sister Chromatid Exchanges and Cell Cycle Kinetics in Alzheimer's Disease," *Biological Psychiatry* 19: 319-327 (1984).
Mecocci P, Polidori MC, Ingegni T, Cherubini A, Chionne F, Cecchetti R, and Senin U, "Oxidative damage to DNA in lymphocytes from AD patients," *Neurology*, 51: 1014-1017 (1998).
Melaragno MI, Smith MDA, Kormann-Bortolotto MH, and Neto JT, "Lymphocyte Proliferation and Sister Chromatid Exchange in Alzheimer's Disease," *Gerontology*, 37: 293-298 (1991).
Mosmann T., "Rapid Colorimetric Assay for Cellular Growth and Survival: Application to Proliferation and Cytotoxicity Assays," *Journal of Immunological Methods*, 65: 55-63 (1983).
Nagy ZS, Esiri MM, and Smith AD, "The Cell Division Cycle and the Pathophysiology of Alzheimer's Disease," *Neuroscience*, 87: 731-739 (1998).
Payao SL, Smith MdA and Bertolucci PH, "Differential Chromosome Sensitivity to 5-Azacytidlne in Alzheimer's Disease," *Gerontology* 44: 267-271 (1998).
Schafer AJ and Hawkins JR, "DNA variation and the future of human genetics," *Nature Biotechnology* vol. 16, pp. 33-39 (1998).
Sherr CJ, "Growth Factor-Regulated G1 Cyclins," *Polyfunctionality of Hemopoietic Regulators: The Metcalf Forum, Stem Cells*, 12 (suppl 1): 47-57 (1994).
Tatebayashi Y, Takeda M, Kashiwagi Y, Okochi M, Kurumadani T, Sekiyama A, Kanayama G, Hariguchi S, and Nishimura T, "Cell-Cycle-Dependent Abnormal Calcium Response in Fibroblasts from Patients with Familial Alzheimer's Disease," *Dementia*, 6: 9-16 (1995).
Trieb K, Ransmayr G, Sgonc R, Lassmann H, and Grubeck Loebenstein B, "APP Peptides Stimulate Lymphocyte Proliferation in Normals, but Not in Patients With Alzheimer's Disease," *Neurobiology of Aging*, 17: 541-547 (1996).
Wagner EF, Hleb M, Hanna N, and Sharma S, "A Pivotal Role of Cyclin D3 and Cyclin-Dependent Kinase Inhibitor p27 in the Regulation of IL-2-, IL-4-, or IL-10-Mediated Human B Cell Proliferation," *Journal of Immunology* 161: 1123-1131 (1998).
Araga S, Kagimoto H, Funamoto K and Takahashi K "Lymphocyte Proliferation and Subpopulations in Dementia of the Alzheimer Type," *Jpn J Med* 29: 572-5 (1990).
Fong CT and Brodeur GM "Down's Syndrome and Leukemia: Epidemiology, Genetics, Cytogenetics and Mechanisms of Leukemogenesis," *Cancer Genet. Cytogenet*. 28: 55-76 (1987).
McKhann, G. et al., "Clinical diagnosis of Alzheimer's disease: Report of the NINCDS-ADRDA Work Group* under the auspices of Department of Health and Human Services Task Force on Alzheimer's Disease" *Neurology* 34: 939-944 (1984).
Nagy Z, Esiri MM, Hindley NJ, Joachim C, Morris JH, King EM-F, McDonald B, Litchfield S, Bametson L, Jobst KA and Smith AD "Accuracy of Clinical Operational Diagnostic Criteria for Alzheimer's Disease in Relation to Different Pathological Diagnostic Protocols," *Dementia* 9: 219-226 (1998).
Nagy-b Z, Combrinck M, Budge M, McShane R, "Cell cycle kinesis in lymphocytes in the diagnosis of Alzheimer's disease," Neurosci. Lett. 317:81-84 (Jan. 2002).
Stieler JT Lederer C, Bruckner MK, Wolf H, Holzer M, Gertz H-J, Arendt T, "Impairment of mitogenic activation of peripheral blood lymphocytes in Alzheimer's disease," NeuroReport 12:3969-3972 (Dec. 2001).

(Continued)

*Primary Examiner* — Michael Burkhart
(74) *Attorney, Agent, or Firm* — Jeffrey I. Auerbach; The Auerbach Law Firm, LLC

(57) ABSTRACT

The present invention relates diagnostic screens for Alzheimer's disease, and in particular to diagnostic tests based on screening for the presence of cellular changes that occur early in the pathology of Alzheimer's disease.

24 Claims, 13 Drawing Sheets

OTHER PUBLICATIONS

Urcelay E, Ibarreta O, Parrilla R, Ayuso MS, Martin-Requero A, "Enhanced proliferation of lymphoblasts from patients with Alzheimer dementia associated with calmodulin-dependent activation of the Na+/H+ Exchanger," Neurobiol. Dis. 8:289-298 (Apr. 2001).

Nagy, Z. "The dysregulation of the cell cycle and the diagnosis of Alzheimer's disease," Biochim Biophys Acta, vol. 1772 (2006 EPub): pp. 402-406.

Chan, S. "Targeting the mammalian target of rapamycin (mTOR): a new approach to treating cancer," Brit. J. of Caner, vol. 91: pp. 1420-1424 (2004).

Wendel, H. et al., "Survival signalling by Akt and elF4E in oncogenesis and cancer therapy," Nature, vol. 428: pp. 332-337 (2004).

Houtgraaf, J. et al., "A concise review of DNA damage checkpoints and repair in mammalian cells," Card. Revascular. Med., vol. 7: pp. 165-172 (2006).

Callegari, A. et al., "UV irradiation induces a postreplication DNA damage checkpoint," Proc. Natl. Acad. Sci. (U.S.A.) 103: pp. 15877-15882 (2006).

Ichimura, K. et al., "Deregulation of the p14ARF/MDM2/p53 Pathway Is a Prerequisite for Human Astrocytiv Gliomas with G1-S Transition Control Gene Abnormalities," Canc. Res., vol. 60: pp. 417-424 (2000).

Dewan, M.J. et al. (1992) "Toward a Definite Diagnosis of Alzheimer's Disease," Comprehensive Psychiatry 33(4):282-290.

Dubois, B. et al. (2007) "Research Criteria for the Diagnosis of Alzheimer's Disease: Revising the NINCDS—ADRDA Criteria," Lancet Neurol. 6:734-746).

* cited by examiner

DIAGNOSTIC SCREENS FOR ALZHEIMER'S DISEASE

CROSS-REFERENCE TO RELATED APPLICATIONS

This application is a continuation-in-part application of U.S. patent application Ser. No. 10/659,578 (filed Sep. 10, 2003;), which application is a 371 national stage application of PCT/GB02/01137 (filed on Dec. 3, 2001, lapsed), both of which applications are herein incorporated by reference in their entirety. This application claims priority to both such applications.

REFERENCE TO SEQUENCE LISTING

This application includes one or more Sequence Listings pursuant to 37 C.F.R. §1.821 et seq., which are disclosed in both paper and computer-readable media, and which paper and computer-readable disclosures are herein incorporated by reference in their entirety.

FIELD OF THE INVENTION

The present invention relates to diagnostic screens for Alzheimer's disease, and in particular to diagnostic tests based on screening for the presence of cellular changes that occur early in the pathology of Alzheimer's disease.

BACKGROUND OF THE INVENTION

As life expectancy increases Alzheimer's disease (AD) is becoming a major health problem in the western world. There has been intensive research aimed at identifying a reliable cure or preventive measures for the disease, so far withput success.

One of the biggest problems in the design and testing of any therapeutic agent is the lack of reliable clinical diagnostic criteria that could identify AD sufferers early enough for any meaningful intervention. However, the currently available clinical diagnostic tools do not allow an accurate and reliable diagnosis of Alzheimer's disease in other than severely demented patients. Furthermore they do not allow the identification of subjects with pre-clinical Alzheimer's disease who could benefit from preventive intervention.

The most often used clinical diagnostic criteria are the NINCDS/ADRDA criteria (McKhann, G. et al., (1984) Neurology 34: 939-944), originally designed for research purposes. These criteria are highly sensitive but have a low specificity. This is due to the fact that the positive predictive value of a diagnosis of "probable" or "possible" Alzheimer's disease is very high, but the negative predictive value is very low (13). In other terms, if a patient fulfils the requirements of the NINCDS/ADRDA criteria for Alzheimer's disease it is highly likely that the patient indeed has got Alzheimer's disease. However, a proportion of the patients who do not fulfill these criteria (e.g. are regarded as controls) are found to have Alzheimer's disease at post mortem examination (13).

As a consequence of their low specificity, the NINCDS/ADRDA criteria are not ideal for clinical diagnostic purposes. Additionally they are not suitable as diagnostic criteria for clinical trials looking at preventive or curative therapies that may have their best chance of being effective if used before significant dementia has developed. Thus there remains a need for a reliable diagnostic test for Alzheimer's disease, and in particular for a test which may be used in the early detection of subjects with pre-clinical Alzheimer's disease who could benefit from preventive intervention.

In recent years it is becoming more widely accepted that the pathogenic basis of Alzheimer's disease is the aberrant re-entry of different neuronal populations into the cell division cycle (14). In healthy elderly individuals rapid cell cycle arrest and re-differentiation may follow this cell cycle re-entry. In contrast, in individuals with Alzheimer's disease the regulatory mechanisms appear to fail and the neurons progress into the late stages of the cell cycle leading to the accumulation of AD-related pathology and/or neuronal death (14).

Studies by the present inventor and others indicate that the cell cycle regulatory failure in Alzheimer's disease occurs at the G1/S transition checkpoint (3). Previous studies on fibroblasts and lymphocytes from Alzheimer's disease patients indicate that the regulation of the cell division cycle might be disrupted in cells other than neurons in this condition (8, 9, 17). It is also known that Alzheimer's disease patients are more prone to some forms of cancer (4) and that Down's syndrome patients, who develop AD in early adult life, are more prone to leukaemia than the general population (7, 10). It is plausible therefore to hypothesis that the cell cycle regulatory failure in neurons, even in early (pre-clinical) stages of AD, might be reflected by similar cell cycle regulatory malfunction in lymphocytes.

The present inventor has now shown that the in vitro responsiveness of lymphocytes to G1 inhibitor treatment is significantly less effective in Alzheimer's disease patients than in control subjects. Additionally, in subjects showing clinical signs of incipient Alzheimer's disease the lymphocyte-response is similar to that seen in Alzheimer's disease patients. These findings represent direct evidence to support the hypothesis that the failure of the G1/S transition control is not restricted to neurons in Alzheimer's disease patients, but also occurs in peripheral cells, such as lymphocytes.

The observation that the regulatory defect at the G1/S transition also occurs in peripheral cells provides the basis for new clinical tests, useful in the diagnosis of Alzheimer's disease, that rely on eliciting the activation of the G1/S transition checkpoint in non-neuronal cells, such as lymphocyte cultures. Since cell cycle regulatory failure in neurons appears to be a very early event in the pathogenesis of Alzheimer's disease, it is anticipated that such tests will be of use for the identification of subjects in the pre-clinical stages of Alzheimer's disease who do not fulfill the requirements of the NINCDS/ADRDA criteria for dementia, but would benefit from early intervention with preventive measures for Alzheimer's disease.

SUMMARY OF THE INVENTION

The present invention relates to diagnostic screens for Alzheimer's disease, and in particular to diagnostic tests based on screening for the presence of cellular changes that occur early in the pathology of Alzheimer's disease.

In detail, the invention provides a method for aiding in a diagnosis of a neurological condition in a human subject, wherein the neurological condition is selected from the group consisting of:

Alzheimer's disease; incipient Alzheimer's disease; possible Alzheimer's disease; and Alzheimer's disease associated with evidence of other type of dementia;

wherein the method comprises the steps of:
(A) determining the effectiveness of the G1/S cell cycle checkpoint exhibited by a non-neuronal cell of the subject; and
(B) comparing the determined G1/S cell cycle checkpoint effectiveness with the G1/S cell cycle checkpoint effectiveness exhibited by a non-neuronal reference cell of a healthy individual or of an individual having the neurological condition to thereby determine whether a defect exists in the effectiveness of G1/S cell cycle checkpoint exhibited by the subject;
whereby the presence of the defect is indicative of the neurological condition in the subject and thereby aids in the diagnosis of the neurological condition.

The invention also includes the embodiment of such method wherein the neurological condition is Alzheimer's disease.

The invention also includes the embodiment of such methods wherein the step (A) is carried out by inducing cell division in the non-neuronal cell and testing responsiveness of the non-neuronal cell of the subject to a cell division G1 inhibitor substance, wherein reduced responsiveness to the cell division G1 inhibitor substance by the non-neuronal cell of the subject relative to that of a non-neuronal reference cell of a healthy individual indicates decreased effectiveness of the G1/S cell cycle checkpoint.

The invention also includes the embodiment of such method wherein the responsiveness of the non-neuronal cell of the subject to the cell division G1 inhibitor substance is determined by:
(A) a cell proliferation assay, wherein higher proliferative activity in the non-neuronal cell of the subject following treatment with the cell division G1 inhibitor substance relative to that of a non-neuronal reference cell of a healthy individual indicates decreased effectiveness of the G1/S cell cycle checkpoint;
(B) calculating the relative lengthening of the G1 phase of the cell cycle in the non-neuronal cell of the subject, wherein a reduced relative lengthening of the G1 phase following treatment with the cell division G1 inhibitor substance relative to that of a non-neuronal reference cell of a healthy individual indicates decreased effectiveness of the G1/S cell cycle checkpoint;
(C) analysis of expression of a cell cycle regulatory protein or an mRNA encoding a cell cycle regulatory protein. The invention particularly includes the embodiment of such methods wherein the cell cycle regulatory protein is selected from the group consisting of CDKN3, p15ink4B, p16ink4A, p19ink4D, p27kip1, p21cip1, p57kip2 and TP53;
(D) assessment of cell viability or cell death, wherein increased cell survival or a reduced degree of cell death in the non-neuronal cell of the subject following treatment with the cell division G1 inhibitor substance relative to that of a non-neuronal reference cell of a healthy individual indicates decreased effectiveness of the G1/S cell cycle checkpoint;
(E) analysis of expression of a cell death related protein or an mRNA encoding a cell death related protein. The invention particularly includes the embodiments of such methods wherein the cell death related protein is a member of the bcl-2 family of proteins; or
(F) assessment of DNA content of the non-neuronal cell of the subject with or without cell cycle analysis.

The invention also includes the embodiment of such methods wherein the step (A) is carried out by inducing cell division in the non-neuronal cell and testing responsiveness of the non-neuronal cell of the subject to a stimulus that induces G1 cell cycle arrest, wherein a reduced responsiveness to the stimulus by the non-neuronal cell of the subject relative to that of a non-neuronal reference cell of a healthy individual indicates decreased effectiveness of the G1/S cell cycle checkpoint.

The invention particularly includes the embodiments of such method wherein the stimulus that induces G1 cell cycle arrest is:
(A) oxidative stress, ionizing radiation, hypoxia, or UV radiation;
(B) DNA damage and the responsiveness of the non-neuronal cell of the subject to the stimulus is determined by analysis of expression of a DNA damage-response element. The invention particularly includes the embodiment of such methods wherein the DNA damage-response element is selected from the group consisting of TP53, Gadd34, Gadd45A, Gadd45B, Gadd45G, Gadd153 and PCNA;

The invention also includes the embodiments of such methods wherein the responsiveness of the non-neuronal cell of the subject to the stimulus that induces G1 cell cycle arrest is determined by:
(A) a cell proliferation assay, wherein higher proliferative activity in the non-neuronal cell of the subject following exposure to the stimulus that induces G1 cell cycle arrest relative to that of a non-neuronal reference cell of a healthy individual indicates decreased effectiveness of the G1/S cell cycle checkpoint;
(B) calculating the relative lengthening of the G1 phase of the cell cycle in the non-neuronal cell of the subject, wherein a reduced relative lengthening of the G1 phase following exposure to the stimulus that induces G1 cell cycle arrest relative to that of a non-neuronal reference cell of a healthy individual indicates decreased effectiveness of the G1/S cell cycle checkpoint;
(C) assessment of cell viability or cell death, wherein increased cell survival or a reduced degree of cell death in the non-neuronal cell of the subject following exposure to the stimulus that induces G1 cell cycle arrest relative to that of a non-neuronal reference cell of a healthy individual indicates decreased effectiveness of the G1/S cell cycle checkpoint;
(D) analysis of expression of a cell death related protein or an mRNA encoding a cell death related protein, especially wherein the cell death related protein is a member of the bcl-2 family of proteins; or
(E) assessment of DNA content of the non-neuronal cell of the subject with or without cell cycle analysis.

The invention particularly includes the embodiments of all such methods wherein the non-neuronal cell of the subject is a lymphocyte.

BRIEF DESCRIPTION OF THE DRAWINGS

The invention will be further understood by reference to the following experimental examples, together with the accompanying Figures, in which.

KEY TO FIGURES

Figure 1:
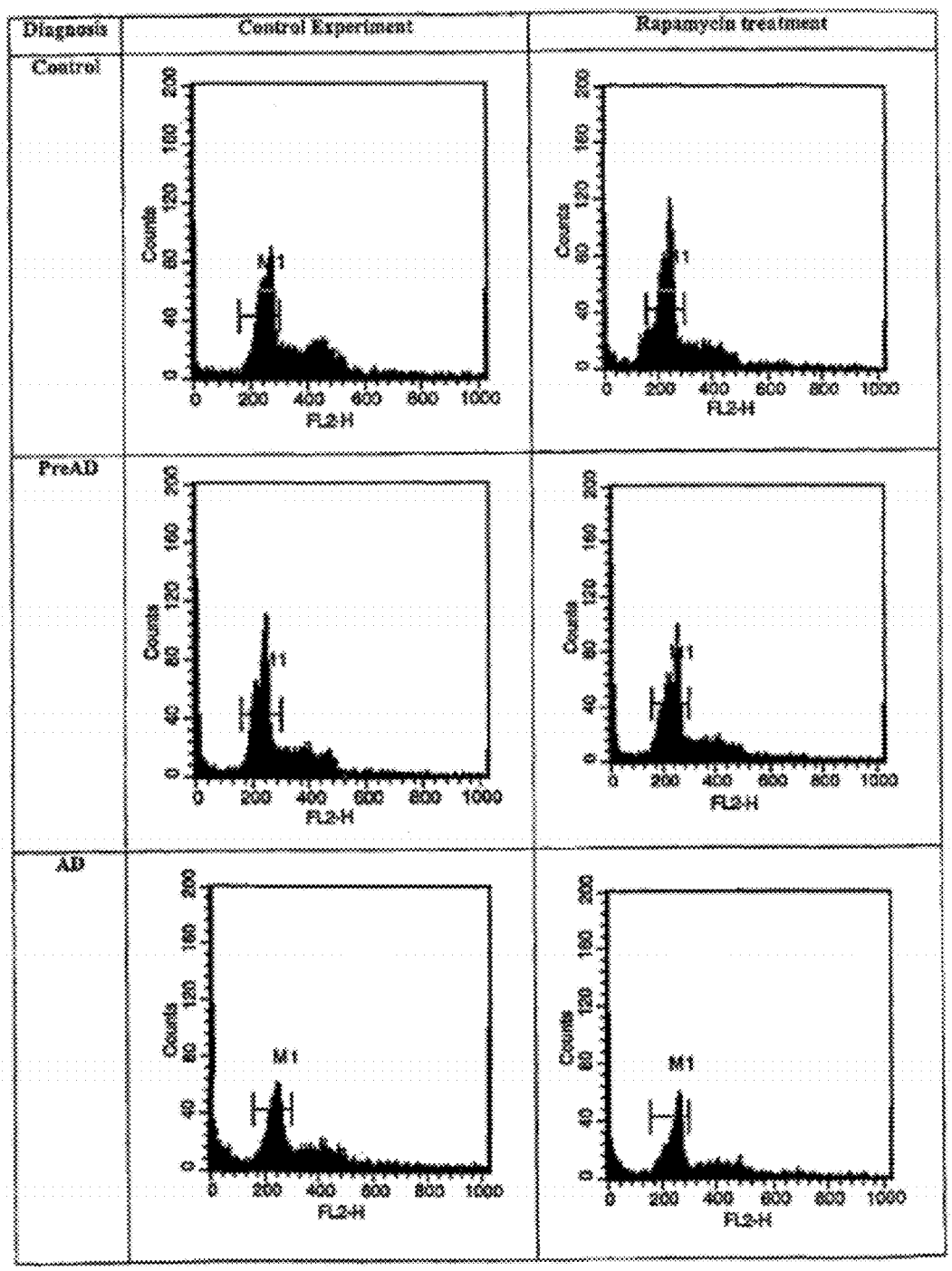
FIG. 1 illustrates flow cytometer readouts for cultured lymphocytes from a control subject, preAD subject and AD patient. Results are shown for both rapamycin treated cells and control, untreated cells. G1 indicates that the cells are in the G1 phase of the cell cycle.

Control: healthy individuals with normal cognitive and neuropsychological test results;
PreAD: healthy individuals with neuropsychological test results suggestive of incipient AD;
PossAD: possible Alzheimer's disease as diagnosed by the NINCDS criteria;
AD: probable Alzheimer's disease as diagnosed by the NINCDS criteria;
ADM: possible Alzheimer's disease (NINCDS) and evidence of other type of dementia;
DNOS: patients with dementia who do not meet the requirements of the NINCDS criteria for probable Alzheimer's disease.

DETAILED DESCRIPTION OF THE INVENTION

In accordance with a first aspect of the invention there is provided a method for diagnosis of Alzheimer's disease in a human subject which comprises screening for the presence of a cell cycle regulatory defect at the G1/S phase transition in non-neuronal cells of the human subject.

The method of the invention is most preferably carried out in vitro on non-neuronal cells isolated from the human subject to be tested. The non-neuronal cells may be any non-neuronal cell type which exhibits the same cell cycle regulatory defect at the G1/S phase transition as is present in the neurons in Alzheimer's disease. In the most preferred embodiment the method is carried out on lymphocytes isolated from the subject and cultured in vitro. There are obvious practical advantages in being able to test for the presence of the cell cycle regulatory defect in a non-neuronal cell type. The use of lymphocytes is particularly convenient, since they are easily isolated from a blood sample and may be cultured in vitro. Another preferred option is the use of fibroblasts, particularly skin fibroblasts which may be conveniently obtained from a skin biopsy.

When the method of the invention is used diagnostically in a patient who is suffering from cognitive deficit and NOT suffering from cancer, the presence of a defect in cell cycle regulation at the G1/S phase transition in a non-neuronal cell type is taken as an indication that the subject has Alzheimer's disease. Typically, a reduction in the effectiveness of the checkpoint control at the G1/S transition is taken as an indication that the subject has Alzheimer's disease.

The availability of a reliable test for a defect underlying the pathology of Alzheimer's disease will significantly improve the ability to diagnose the condition, and in particular will enable early diagnosis. The currently available operational diagnostic criteria for Alzheimer's disease only allow diagnosis of possible or probable AD very late, when dementia is already present. A definite diagnosis of Alzheimer's disease can only be made after post mortem examination. It is apparent from the work of the present inventor that a defect in cell cycle control is detectable in peripheral (non-neuronal) cells, such as lymphocytes, well before the clinical signs of fully developed dementia appear. Hence, the method of the invention provides a tool for early diagnosis of Alzheimer's disease, especially detection of individuals who are in pre-clinical stages of the disease, and for identification of individuals who have not yet developed Alzheimer's disease as such but are "at risk" of doing so because of the presence of the cell cycle regulatory defect. This opens up the possibility of early intervention with preventive measures, including, inter alia, changes in life style and vitamin regimes and HRT for post menopausal women.

100481 The availability of diagnostic tools capable of detecting early changes in individuals who have not yet developed Alzheimer's disease as such will also facilitate the development and testing of therapies aimed at stopping the progression of the disease at a point before the development of significant brain pathology. The diagnostic tests may also be applied in the development of animal models of early Alzheimer's disease, for example in the identification of a mouse model which exhibits an analogous defect in cell cycle regulation to that present in Alzheimer's disease.

The ability to identify individuals having a cell cycle regulatory defect at the G1/S transition may be applied to the selection of individuals to be included in clinical trials. Clinical trials are more likely to produce meaningful results if the individuals included in the trial are selected to be those most likely to benefit from the treatment under test.

The identification of G1/S regulatory defect in lymphocytes taken from a patient suffering from incipient or full blown Alzheimer's disease may indicate the presence of immune problems in the patient, or a likelihood that the patient will develop immune problems as the disease progresses. The availability of such information will assist the clinician in deciding whether to intervene with therapy aimed at alleviating/preventing immune problems complicating the Alzheimer's disease.

The method of the invention is particularly preferred for diagnosis of sporadic Alzheimer's Disease. However, it would also be useful in the diagnosis of forms of Familial Alzheimer's Disease which exhibit an equivalent cell cycle regulatory defect. Generally this will not include Familial Alzheimer's Disease associated with presenilin-1 or presenilin-2 mutations.

There are several ways in which to screen for the presence of a cell cycle regulatory defect at the G1/S phase transition in non-neuronal cells in accordance with the invention. In one embodiment screening for the presence of the cell cycle regulatory defect may be accomplished by first inducing the cells to divide, then inducing cell cycle arrest by addition of a cell division inhibitor substance and testing the responsiveness of the cells' G1/S cell cycle regulatory mechanisms to the addition of the cell division inhibitor substance.

Most preferably the cell division inhibitor substance will be a specific G1 inhibitor, for example rapamycin. Cell division may be induced by the addition of a mitogenic stimulus, for example one or more growth factors. If the test is carried out using lymphocytes, then phytohaemaglutinin may be used to induce cell division.

In a further, related embodiment treatment with the cell division inhibitor substance may be replaced by treatment with a stimulus which induces cell cycle arrest at G1, for example an environmental stimulus. Screening for the presence of the G1/S regulatory defect is therefore accomplished by: inducing the cells to divide, exposing the cells to a stimulus which induces cell cycle arrest at G1 and testing the responsiveness of the G1/S cell cycle regulatory mechanisms of the cells to the addition of the stimulus which induces cell cycle arrest.

Suitable stimuli of cell cycle arrest include, inter alia, ionizing radiation, hypoxia, UV radiation, etc. In a preferred embodiment, cell cycle arrest may be induced by treatment of the cells with $H_2O_2$ to produce oxidative stress. As above, cell division may be induced by the addition of a mitogenic stimulus, for example one or more growth factors. Phytohaemaglutinin may be used to induce cell division in cultured lymphocytes.

The rationale behind both of these methods is to first stimulate the cells to divide, then attempt to arrest the cell cycle at the G1 stage using either a cell division inhibitor or other stimulus inducing cell cycle arrest and then evaluate the effect of such treatment on the cell cycle regulatory system. The effect on cell cycle regulation may be evaluated by a variety of different means, as discussed below. The treatment with a cell division inhibitor or other stimulus that induces cell cycle arrest may be referred to herein as "cell cycle inhibitory treatment" or "inhibitory treatment." If a cell cycle regulatory defect at the G1/S transition is present then this will affect the responsiveness of the cells to attempted cell cycle arrest. In general, the presence of a cell cycle regulatory defect at G1/S results in a reduced responsiveness to treatment with a cell division inhibitor or other stimulus that induces cell cycle arrest at G1, i.e. the inhibitory treatment is less effective in arresting the cell cycle at the G1/S checkpoint in cells with such a defect.

Various approaches may be implemented before and after the addition of the mitogenic stimulus and before and after the attempted arrest of the cell cycle to test the responsiveness of the cells to cell cycle inhibitory treatment. A non-exhaustive list of preferred approaches which may be used in accordance with the invention is given below, other suitable approaches will be known to persons skilled in the art:

(1) Proliferation assay performed in order to assess whether cell cycle arrest has occurred and to what extent as a result of inhibitory treatment. The proliferation assay may be carried out according to any of the standard protocols known in the art. A particularly suitable example is the MTT survival assay (commercially available from Chemicon International Ltd, see Mosmann, T. In J. Immunol. Methods, 1983, vol: 65, 55-63).

In a typical screen proliferation assays are performed on both cells treated with a cell division inhibitor or other stimulus inducing cell cycle arrest and untreated control cells from the same subject. Since the inhibitory treatment will be effective only in the presence of an intact G1/S regulatory system, the difference in degree of proliferation between the treated and untreated cells will be significantly smaller in Alzheimer's disease patients than in age matched control individuals. In general, little or no change in the proliferative activity of cells from the subject in the presence of inhibitory treatment indicates a reduced responsiveness to cell cycle inhibition in the G1 phase, and hence the presence of a regulatory defect at the G1/S transition. The presence of such a regulatory defect is in turn taken as an indication that the subject has Alzheimer's disease.

(2) Calculating the relative lengthening of the G1 phase of the cell cycle in cells from the subject as a result of exposure to a cell division inhibitor or stimulus that induces cell cycle arrest. The relative lengthening of the G1 phase as a result of exposure to the cell division inhibitor or stimulus that induces cell cycle arrest is calculated using the formula RL=100f-100 (expressed as a percent). "f" is the ratio of the time in G1 for cells (non-neuronal cells from the subject under test) exposed to inhibitory treatment with the cell division inhibitor or stimulus that induces cell cycle arrest ($TG1_{tr}$) versus the time in G1 for untreated control cells (i.e. also non-neuronal cells from the subject under test) not exposed to inhibitory treatment ($TG1_c$). "f" may be calculated according to the following relation:

$$f=TG1_{tr}/TG1_c=[1n2-1n(2-G1_{tr})][1n(2-G1_c)]/[1n(2-G1_{tr})][1n2-1n(2-G1_c)] \quad (5)$$

Various techniques may be employed to obtain the values of $TG1_{tr}$ and $TG1_c$. In a preferred embodiment $TG1_{tr}$ and $TG1_c$ may be obtained by determining the proportion of cells in the various phases of the cell cycle for both treated cells (non-neuronal cells from the test subject treated with the cell division inhibitor substance or stimulus that induces cell cycle arrest) and untreated control cells (non-neuronal cells from the same subject not exposed to the cell division inhibitor substance or stimulus that induces cell cycle arrest). The proportion of cells in the various phases of the cell cycle may be readily determined by incorporation of a labeled nucleotide analogue, preferably bromodeoxyuridine (BrdU), followed by fluorescence activated cell sorting (FACS analysis), or equivalent, as described in the accompanying examples.

The presence of a cell cycle regulatory defect at the G1/S phase transition is indicated by a reduced relative lengthening of the G1 phase in the presence of the cell division inhibitor substance or stimulus in cells from the test subject, as compared to control cells not having a cell cycle regulatory defect at the G1/S phase transition (see under (1) for further definition of suitable control cells). The control cells not having a cell cycle regulatory defect at the G1/S phase transition are not to be confused with the "untreated control" cells used for calculation of RL, which are cells from the test subject which have not been exposed to inhibitory treatment.

(3) Assessment of cell cycle regulatory protein or mRNA expression. Expression of cell cycle regulatory proteins may be assessed using standard techniques well known in the art such as, for example, immunoblotting, western blotting, ELISA or related methods. Assessment of expression of corresponding mRNAs encoding the cell cycle regulatory proteins may also be accomplished by means of standard methods such as, for example, hybridization techniques, "DNA chip" analysis or related methods or amplification-based techniques such as RT-PCR or nucleic acid sequence-based amplification (NASBA). Suitable methods for the detection/quantitation of mRNAs which may be used in accordance to the invention will be well known to those skilled in the art. Certain of these methods, for example RT-PCR, rely on detection/quantitation of a cDNA copy of the relevant mRNA.

The cell cycle regulatory defect present in Alzheimer's disease may result in changes in the pattern of expression of cell cycle regulatory proteins, and their corresponding mRNAs. Screening for changes in expression of particular cell cycle regulatory proteins and/or the corresponding mRNAs may therefore be used diagnostically to identify the presence of a cell cycle regulatory defect at G1/S. In addition, expression of cell cycle regulatory proteins may be used as a marker of progression through the cell cycle. Hence, the responsiveness of cells to inhibitory treatment may be assessed by looking at the expression of one or more cell cycle regulatory proteins, in order to determine the extent to which inhibitory treatment causes cell cycle arrest in cells from the test subject. Suitable cell cycle regulatory proteins include CDKN3, p15ink4B, p16ink4A, p19ink4D, p27kip1, p21cip1, p57kip2 and TP53. The sequences of these proteins, and the genes encoding them, are publicly available. A list of OMIM accession numbers for these proteins is provided in the accompanying Examples (Table 16); Antibodies useful in the detection of each of these proteins are available commercially.

(4) Assessment of cell viability and cell death by any method known in the art. When a proliferating cell is arrested in the G1/S transition one of two possible "downstream" phenomena may result, either differentiation or programmed cell death. These downstream phenomena may be used as an indication of the presence in a cell population of a regulatory defect at the G1/S transition, since if regulation of the G1/S transition is defective then the downstream effects of cell cycle arrest at G1/S will also be abnormal. A lower degree of cell death or higher degree of cell viability in response to inhibitory treatment in cells from the test subject, as compared to control cells, is taken as an indication that the subject has Alzheimer's disease.

(5) Assessment of cell death related (inducing or preventing) protein or mRNA expression using standard techniques. In this embodiment, expression of cell death related proteins, or the corresponding mRNAs, is used as an indirect assessment of the downstream effects of treatment with a cell division inhibitor or other stimulus inducing cell cycle arrest at the G1/S transition. Suitable cell death related proteins include members of the bcl-2 family of proteins, of which there are many known in the art.

(6) Assessment of the expression of DNA damage response element proteins or corresponding mRNAs using standard techniques. This approach may be used when the stimulus used to induce cell cycle arrest at G1/S is DNA damage, for example treatment with a chemical agent which causes DNA damage or exposure to UV radiation. Under normal circumstances the presence of DNA damage will induce a cell to arrest at the G1/S phase transition and attempt to repair the damaged DNA via activation of DNA damage response pathways. Alterations in the pattern of expression of proteins involved in the normal response to DNA damage, or the corresponding mRNAs, in response to the presence of damaged DNA may therefore be used as an indication of the presence of a cell cycle regulatory defect at the G1/S phase transition. Suitable DNA damage response elements include TP53, Gadd34, Gadd45A (126335), Gadd45B (604948), Gadd45G (604949), Gadd153 (126337) and PCNA (176740). A list of OMIM accession numbers for these DNA damage response elements is provided below.

(7) Assessment of the DNA content of the non-neuronal cells, with or without cell cycle analysis. In this embodiment, measurement of the DNA content of cells from the test subject treated with a cell division inhibitor or other stimulus inducing cell cycle arrest provides an indirect indication of the presence of a regulatory defect at the G1/S transition in such cells. The rationale behind this method is the difference in DNA content between cells in the G1 phase and cells in the G2 phase which have passed through the DNA replication stage of the cell cycle. When a population of normal cells (i.e. without a regulatory defect at G1/S) are treated to induce cell cycle arrest in G1 or at G1/S, the majority of the cells will remain in the G1 phase. However, if cells have a regulatory defect at G1/S, a proportion of the cells will pass through the G1/S checkpoint and undergo DNA replication. Thus an increased DNA content in cells from a test subject, as compared to control cells not having a regulatory defect at G1/S, following treatment to induce cell cycle arrest at G1 is taken as an indication of the presence of a regulatory defect at G1/S.

The presence of such a regulatory defect is in turn taken as an indication that the subject has Alzheimer's disease.

The above list of techniques suitable for use in testing the responsiveness of non-neuronal cells, particularly cultured lymphocytes, to inhibitory treatment with a cell division inhibitor or stimulus that induces cell cycle arrest is intended to be illustrative of rather than limiting to the invention.

In a second aspect the invention provides a method for use in diagnosis of Alzheimer's disease in a human subject which comprises screening for the presence in the genome of said subject of at least one mutation or allelic variant in a cell cycle regulatory gene, wherein the presence of a mutation or allelic variant in a cell cycle regulatory gene is taken as an indication of Alzheimer's disease.

Most preferably, the method of the invention will involve screening for the presence of at least one mutation or allelic variant in a cell cycle regulatory gene selected from the group consisting of CDKN3, p15ink4B, p16ink4A, p19ink4D, p27kip1, p21cip1, p57kip2 and TP53.

The method of the invention is not limited to screening for the presence of any specific mutation or genetic variant, although screening for the presence of specific mutations/variants shown to be associated with Alzheimer's disease is contemplated. The invention encompasses scanning the cell cycle regulatory gene, or a sub-region thereof, for the presence of mutations or genetic variants, including previously unknown mutations/variants. For the avoidance of doubt, the term "gene" includes the regulatory regions, in particular the promoter region. The presence of one or more mutations or genetic variants in a cell cycle regulatory gene, particularly mutations/variants which result in a change in the amino acid sequence of the protein encoded by the gene or which alter the function of the encoded protein or which alter the level of expression of the protein, is taken as an indication that the individual has Alzheimer's disease, on the basis that the presence of such a mutation or variant is indicative of a cell cycle regulatory defect.

There are many techniques known in the art for detection of genetic variation which may be used, in accordance with the invention, to scan a cell cycle regulatory gene of a given human subject for the presence of mutations/allelic variants. Suitable techniques include, for example, single strand conformation polymorphism analysis (SSCP), PCR-SSCP heteroduplex analysis (HA), denaturing gradient gel electrophoresis (DGGE), DNA sequencing, RNase cleavage, chemical cleavage of mismatch (CCM) etc. (see review by Schafer and Hawkins, Nature Biotechnology, Vol: 16, pp. 33-39, 1998).

The accompanying Example 2 describes the use of PCR-SSCP to screen for polymorphic variants in the p21cip and p57 genes and thereby identify a polymorphic variant in exon 2 of the p21cip gene and two polymorphic variants in exon 2 of the p57 gene. The same technical approach may be employed to screen for polymorphic variants in other genes with appropriate modification, i.e. the selection of PCR primers specific for the gene of interest.

Scanning for the presence of mutations/allelic variants is carried out on a sample of genomic DNA isolated from the human subject. Genomic DNA may be conveniently isolated from a whole blood sample using standard techniques well known in the art. Advantageously, the process of scanning for the presence of mutations/allelic variants may be carried out on genomic DNA prepared from cultured lymphocytes from the subject. The same culture of lymphocytes may also be tested "functionally" for the presence of a cell cycle regulatory defect at the G1/S phase transition, for example by testing responsiveness to inhibitory treatment using a method according to the first aspect of the invention.

Associations between a given polymorphic variant and susceptibility to Alzheimer's disease may be confirmed by carrying out genetic association studies, for example family-based or case-control association studies. The disease association of particular polymorphic variants may also be determined by evaluating the relationship between genotype and expression of markers of cell cycle progression in the brain. In the accompanying examples, the relationship between genotype and expression of cyclin B (a marker of progression though the cycle to the G2 stage) in neuronal nuclei was evaluated. Other markers of cell cycle progression could have been used with equivalent effect.

In a specific embodiment, the method may involve genotyping for one of the polymorphic variants in the p21 and p57 genes described in the accompanying examples. These variants, denoted p21E2 alleles A and B, p57E2A alleles A and B, and P57E2B alleles A and B, may be genotyped on the basis of PCR-SSCP analysis using the following primer sets under the conditions specified in the accompanying examples:

```
p21E2 A/B:
                                              (SEQ ID NO: 1)
5'-CGGGATCCGGCGCCATGTCAGAACCGGC-3'
and (SEQ ID NO: 2)
5'-CCAGACAGGTCAGCCCTTGG-3'

P57E2A A/B:
                                              (SEQ ID NO: 3)
5'-GGCCATGTCCGACGCGTC-3'
and (SEQ ID NO: 4)
5'-AGGCGGCAGCGCCCCACCTG-3' p57E2B A/B:
                                              (SEQ ID NO: 5)
5'-ATTACGACTTCCAGCAGGACATG-3'
and (SEQ ID NO: 6)
5'-CTGGAGCCAGGACCGGGACTG-3'
```

Figure 18:
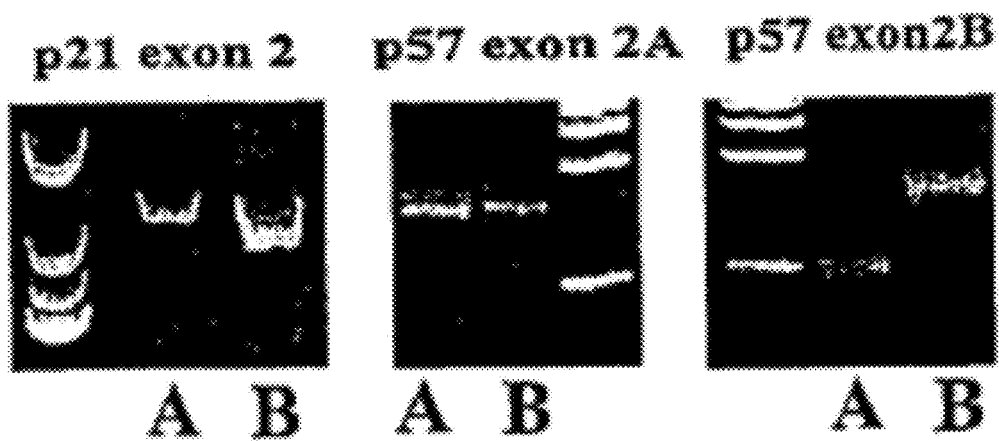
FIG. 18 illustrates the result of PCR-SSCP screening for polymorphisms in exon 2 of p21 and exon 2 of p57 and exon fragments 2A and 2B.

In each case, the A and B alleles may be identified on the basis of differential electrophoretic mobility of the resultant PCR products under the conditions defined in Example 2, with reference to FIG. 18. It is, however, not intended to limit the invention to the use of PCR-SSCP and other methods of genotyping the same variants may be used.

The p21E2 A allele and the p57E2A A allele are both associated with increased progression through the G1/S checkpoint, and therefore with susceptibility to Alzheimer's disease.

Screens based on detection of the presence of mutations or allelic variants in genes encoding cell cycle regulatory genes may involve genotyping for two or more polymorphic variants, or may involve scanning one or more cell cycle regulatory genes for the presence of genetic variation. Any genetic variation which has an adverse effect on the function of a cell cycle regulatory gene may potentially result in by-pass of the G1/S transition check point, and consequential AD pathology. Accumulation of genetic variation within a single regulatory gene, or across multiple genes, may have an additive effect.

Screens based on detection of the presence of mutations or allelic variants in genes encoding cell cycle regulatory genes may be used in the diagnosis of Alzheimer's disease, possibly in conjunction with other diagnostic tests, such as screening for the presence of a cell cycle regulatory defect. They may also be used in order to identify individuals having a predisposition to Alzheimer's disease because of the presence of the mutation(s) or allelic variant(s) in a cell cycle regulatory gene.

The approach of screening for mutations or allelic variants in a cell cycle regulatory gene may also be used in order to determine any genetic basis for Alzheimer's disease in a patient previously diagnosed with Alzheimer's disease.

In a third aspect, the invention provides a method for use in diagnosis of Alzheimer's disease in a human subject which comprises screening for the presence in the genome of said subject of at least one mutation or allelic variant in a gene encoding a DNA repair enzyme, wherein the presence of a mutation or allelic variant in such a gene is taken as an indication of Alzheimer's disease.

Suitable genes include those encoding the DNA repair enzymes Ku70, Ku80, Ku86, NDHII, BLM, RECQL, RECQL4 and RECQL5. The term "gene" includes the regulatory regions, in particular the promoter region.

Again, the method of the invention does not require screening for the presence of any particular mutation or genetic variant, although screening for the presence of particular mutants/variants associated with Alzheimer's disease is contemplated. The method may involve scanning the gene encoding a DNA repair enzyme, or a sub-region of such a gene, for the presence of any mutation or genetic variant, including previously unknown mutations/variants.

The presence of one or more mutations or genetic variants in a gene encoding a DNA repair enzyme is taken as an indication of Alzheimer's disease, because the DNA repair enzymes act on pathways related to cell cycle regulation. The presence of mutations or allelic variants in genes encoding DNA repair enzymes is therefore indirectly indicative of a cell cycle regulatory defect.

The amount of somatic mutations in the brain in AD patients is observed to be significantly associated with cell cycle deregulation and severity of AD-type pathology (see accompanying examples). Therefore, it is suggested that DNA-repair insufficiency may lead to the de-regulation of the G1/S transition point finally leading to the development of Alzheimer's disease.

Screens based on detection of the presence of mutations or allelic variants in genes encoding DNA repair enzymes may be used diagnostically, particularly in the identification of individuals with pre-clinical Alzheimer's disease. Similar screens may also be used to identify individuals who are predisposed to developing Alzheimer's disease because of the presence of mutation(s)/variant(s) in a gene or genes encoding DNA repair enzymes and also to determine any genetic basis for Alzheimer's in a patient previously diagnosed with Alzheimer's disease.

The actual process of screening for the presence of mutations/allelic variants may be carried out using any of the techniques known in the art, as discussed above.

In a still further aspect, the invention provides a method of identifying compounds having potential pharmacological activity in the treatment of Alzheimer's disease, which method comprises steps of: analyzing the regulation of the G1/S transition in non-neuronal cells, which cells exhibit a cell cycle regulatory defect at the G1/S phase transition, in the presence and absence of a test compound, wherein a test compound which results in correction of the regulatory defect at the G1/S transition in said cells is identified as having potential pharmacological activity in the treatment of Alzheimer's disease.

The method of the invention may be performed using essentially any non-neuronal cells which exhibit an analogous cell cycle regulatory defect at the G1/S phase transition to that observed in the neurons in Alzheimer's disease. Suitable cells may include cultured lymphocytes derived from an individual, or several individuals, having Alzheimer's disease.

"Analysis" of the regulation of the G1/S transition may be performed using any of the methods described in connection with the first aspect of the invention as suitable for screening for the presence of a cell cycle regulatory defect at G1/S. Advantageously, the method used for analysis of the regulation of the G1/S phase transition will be one capable of being performed in multi-well microtiter plates, allowing the compound screen to be carried out in mid-to-high throughput format. The most preferred method suitable for use in a mid-to-high throughput format is the cell proliferation assay.

Cells exhibiting a regulatory defect at the G1/S transition are exposed to test compounds and the effect of the test compound on regulation of the G1/S transition is assessed with reference to suitable controls, e.g. cells not exposed to any test compound. In a typical screen, the test compound will be tested at a range of different concentrations.

There is no limitation on the types of candidate compounds to be tested in the screening methods of the invention. Test compounds may include compounds having a known pharmacological or biochemical activity, compounds having no such identified activity and completely new molecules or libraries of molecules such as might be generated by combinatorial chemistry. Compounds which are DNA, RNA, PNA, polypeptides or proteins are not excluded.

The basic compound screening methodology may also be adapted for use in assessing the efficacy of a form of treatment for Alzheimer's disease, for example to test the effect of a particular pharmacological agent on cell cycle regulation.

In a useful variation, the method of the invention may be used specifically to determine whether a pharmacological agent is likely to be of benefit in the treatment of Alzheimer's disease in a particular human individual. In this case the assay is performed using non-neuronal cells from the individual that exhibit a cell cycle regulatory defect at the G1/S phase transition, most preferably cultured lymphocytes. The cells are tested for the presence of the defect in regulation at the G1/S phase transition at the G1/s transition in the presence and absence of the pharmacological agent. Pharmacological agents which result in "correction" of the regulatory defect at the G1/S transition are identified as likely to be of benefit in the treatment of Alzheimer's disease in the individual. By "correction" is meant a significant degree of restoration to normal cell cycle regulation. This may be assessed by reference to control cells, for example cells of the same type taken from an age-matched control individual not having Alzheimer's disease or any evidence of a regulatory defect at the G1/S transition or any genetic defect/allelic variation which might be expected to pre-dispose to Alzheimer's disease.

The present invention also provides for pharmaceutical packs or kits for carrying out the assays disclosed herein. In particular, the present invention provides a diagnostic kit for use in screening for the presence of a cell cycle regulatory defect at the G1/S phase transition in non-neuronal cells of a human subject, and for use in diagnosing a human subject with a neurological condition, in particular, Alzheimer's disease. In one embodiment, the kit comprises one or more containers filled with a cell division inducement substance and a cell division inhibitor substance. Additionally, one or more cell proliferation assays or agents useful for measuring cell viability and proliferation may also be included in the pack or kit. By use of the kits of the invention, it is possible to determine the presence of a cell cycle regulatory defect and provide a diagnosis of a neurological condition, in particular, any or all of the neurological conditions: Alzheimer's disease, incipient Alzheimer's disease, possible Alzheimer's disease, and/or Alzheimer's disease associated with some other type of dementia.

Having now generally described the invention, the same will be more readily understood through reference to the following examples, which are provided by way of illustration and are not intended to be limiting of the present invention unless specified.

EXAMPLES

Example 1

Evidence for the Occurrence of a Cell Cycle Regulatory Defect in Lymphocytes of Alzheimer's Disease Patients Materials and Methods The study included 102 subjects who were full participants of the Oxford Project to Investigate Memory and Ageing (OPTIMA). The yearly routine OPTIMA examination includes a physical examination, cognitive and neuropsychological testing. Drug intake and any intercurrent infections are recorded. Blood was collected in lithium heparin or EDTA vacutainers. Lymphocytes were isolated according to a standard protocol using Ficoll (Sigma). In order to standardize the culture methods for all patients the separated lymphocytes were frozen and stored for further analysis.

When the lymphocytes were needed for culture, they were thawed in a 37° C. water bath and washed twice in RPMI (any medium or buffer which supports lymphocyte survival may be used to wash the cells with equivalent effect). Cell viability (Trypan Blue exclusion) was typically approximately 80-90%.

A first set of experiments was carried out on 49 subjects (Table 1A), whilst a second set of experiments was carried out on 55 subjects (Table 1B). In the first set of experiments (49 subjects) two parallel lymphocyte cultures were set up from every individual in RPMI medium supplemented with 10% FCS at a concentration of $1 \times 10^6$ cells per 1 ml of culture media. Phytohaemaglutinin (PHA) was added to the cultures at a final concentration of 22 µg/ml to activate the lymphocytes. Cultures were incubated for 48 hours at 37° C. in a humidified atmosphere containing 5% $CO_2$. After 48 hours incubation one culture was treated with 100 ng/ml rapamycin, while the other untreated culture was kept as a control. After a further 23 hours incubation BrdU was added in a concentration of 10 µg/ml to all cultures. After another hour cultures were 'collected' and fixed in 70% ice-cold ethanol. BrdU incorporation was assessed using immunohistochemistry followed by FACS analysis. The proportion of cells in various phases of the cell cycle was determined and data transformation performed to obtain the relative lengthening of the G1 phase (FIG. 1).

The calculations (relative lengthening of the G1 phase of the cell cycle in treated cultures relative to control cultures) were based on the assumptions that cells were in the exponential phase of proliferation and that the growth fraction in the cultures (ratio of dividing cells versus quiescent cells) was 1.0 (5). It was also assumed that rapamycin only altered the length of the G1 phase (19). Based on these assumptions the relative lengthening of the G1 phase was calculated using the formula: RL=100f-100 (expressed in percent). The ratio of the G1 time in treated versus control cultures:

$$f=TG1_{tr}/TG1_{c}=[1n2-1n(2-G1_{tr})][1n(2-G1_{c})]/[1n(2-G1_{tr})][1n2-1n(2-G1_{c})] \quad (5)$$

In the second set of experiments (53 subjects) after an initial 48 hours incubation (as above) four separate cultures were set up. Control cultures were left without any treatment, one set of cultures was treated with 100 ng/ml rapamycin, the third set was treated with 1 µM doxorubicin while the fourth set was treated with 120 µM $H_2O_2$. Doxorubicin induces DNA damage, leading to arrest at G2/M, rather than G1/S. $H_2O_2$ treatment produces oxidative stress, leading to a reversible and temporary cell cycle arrest at G1/S.

After 20 hours of incubation a 4 hour long MTT survival assay (Chemicon International Ltd) was set up. Results were read using a microplate reader (570 filter; 630 reference filter). The ratio between cell numbers in treated cultures versus controls was expressed as percent.

All experiments were carried out blind to the clinical diagnosis of the patients.

The results were analyzed in relation to the clinical diagnosis provided by the clinicians involved in the OPTIMA project.

Statistical analysis was carried out using the Statgraphics software package. ANOVA tests were performed to examine the effect of the clinical diagnosis on the cell culture parameters. A second set of analyses was also carried out to control for the effect of age on the results. Age correction allows for any age-related variation in the particular parameter under test. The effect of age on a given parameter is determined by looking at the effects of age on the parameter in healthy subjects.

Results

Figure 2:
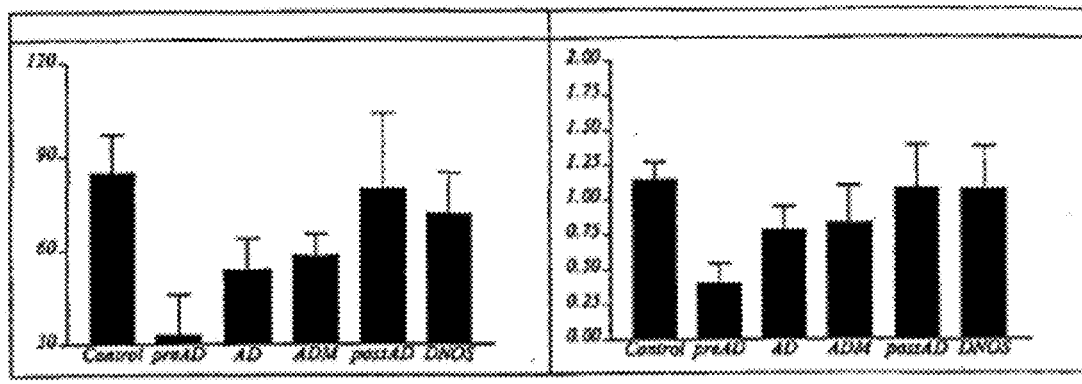
FIG. 2 illustrates relative (left panel) and age-corrected (right panel) lengthening of the G1 phase of the cell cycle under the influence of rapamycin in cultured lymphocytes from preAD, AD, ADM, possAD, DNOS and control subjects.

The clinical diagnoses of the patients included in the two sets of experiments are summarized in Table 1a and Table 1b. The relative lengthening of the G1 phase under the influence of the specific G1 inhibitor rapamycin was significantly dependent on the clinical diagnosis of our patients (Anova p=0.04, Kruskall-Wallis test p=0.017) (FIG. 2). The highest values, indicating more effective G1 inhibition by rapamycin, were found in subjects diagnosed as controls, dementia syndromes other than AD and possible Alzheimer's disease patients. Patients diagnosed as suffering from AD (probable AD by NINCDS) and those with AD and coexisting other pathology (ADM) were found to have a significantly less effective G1 block than control subjects and patients suffering from DNOS or possAD as diagnosed by the NINCDS criteria (FIG. 2). The differences between clinical diagnostic categories are similar even when the relative G1 delay was corrected for age (FIG. 2).

Figure 3:
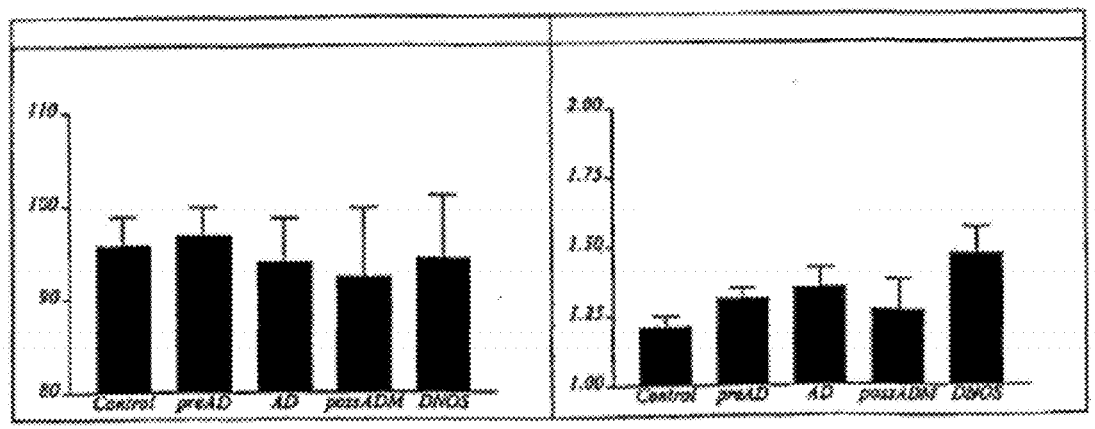
FIG. 3 illustrates the effects of 24 hours rapamycin treatment on cell survival in cultured lymphocytes from preAD, AD, possADM, DNOS and control subjects. Absolute values are shown in the left panel, age-corrected values in the right panel.
Figure 4:
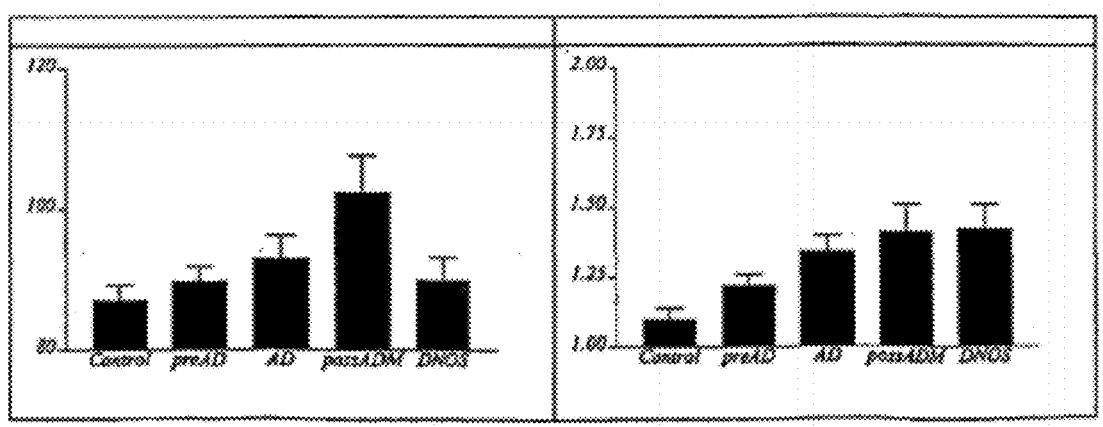
FIG. 4 illustrates the effects of $H_2O_2$ treatment on cell survival in cultured lymphocytes from preAD, AD, possADM, DNOS and control subjects. Absolute values are shown in the left panel, age-corrected values in the right panel.
Figure 5:
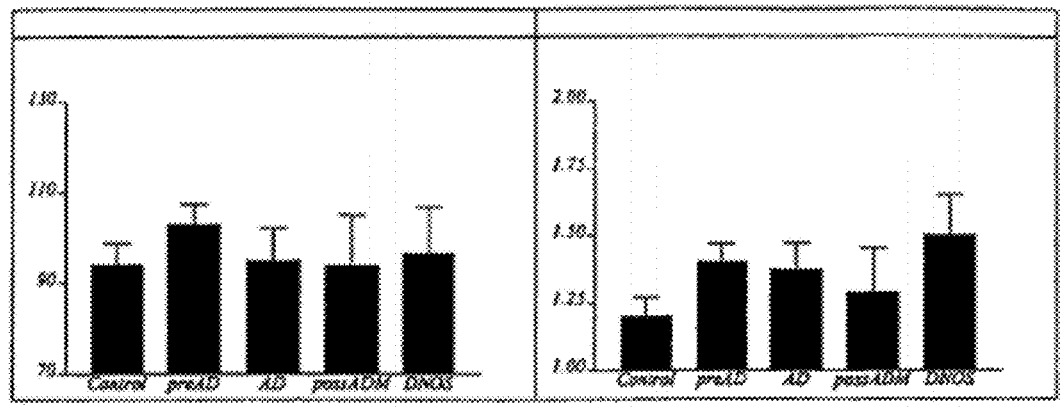
FIG. 5 illustrates the effects of doxorubicin treatment on cell survival in cultured lymphocytes from preAD, AD, possADM, DNOS and control subjects. Absolute values are shown in the left panel, age-corrected values in the right panel.

In the second set of experiments, the cell numbers after rapamycin treatment showed the expected pattern of higher cell numbers in AD and poss AD cultures, as compared to control cultures (FIG. 3). However, the sensitivity of the MTT assay system is relatively low. Doxorubicin treatment did not result in significant differences between patient groups (FIG. 3). In contrast to doxorubicin treatment, the reduction of cell numbers by $H_2O_2$ treatment was dependent upon the clinical diagnosis (FIG. 4). The patients suffering from AD, preAD and possAD had significantly higher cell numbers than control subjects as a result of the $H_2O_2$ treatment. DNOS patients showed wide variations and were not different from either of the other patient groups (FIG. 5).

TABLE 1A

Patients included in this study

| Clinical Diagnosis | No. of Patients |
| --- | --- |
| Control | 14 |
| PreAD | 13 |
| PossAD | 3 |
| AD | 9 |
| ADM | 7 |
| DNOS | 3 |

TABLE 1B

| Clinical Diagnosis | No. of Patients |
| --- | --- |
| Control | 16 |
| PreAD | 18 |
| ADM | 3 |
| AD | 11 |
| DNOS | 5 |

KEY for Tables 1A and 1B:

Control: healthy individuals with normal cognitive and neuropsychological test results;

PreAD: healthy individuals with neuropsychological test results suggestive of incipient AD;

PossAD: possible Alzheimer's disease as diagnosed by the NINCDS criteria;

AD: probable Alzheimer's disease as diagnosed by the NINCDS criteria;

ADM: possible Alzheimer's disease (NINCDS) and evidence of other type of dementia;

DNOS: patients with dementia who do not meet the requirements of the NINCDS criteria for probable Alzheimer's disease.

Data and Analysis

TABLE 2

| Bloodtest ID | Age | Age Of Onset | ApoE4* | ROC For Cutoff | Diagnosis Patent | dG1 | Variable For New DG | Dg Based On Ly Test |
| --- | --- | --- | --- | --- | --- | --- | --- | --- |
| 49 | 72 | 62 | 0 | 1 | AD | 47.908857 | 1.477371188 | AD |
| 33 | 58 | 52 | 0 | 1 | AD | 53.63137 | 3.209527311 | AD |
| 10 | 68 | 61 | 1 | 1 | AD | 0 | 3.957 | AD |
| 25 | 69 | 63 | 1 | 1 | AD | 27.00255 | 2.735177835 | AD |
| 75 | 82 | 78 | 0 | 1 | AD | 44.029948 | 0.231760271 | AD |
| 14 | 67 | 64 | 0 | 1 | AD | 97.068303 | 0.208543783 | AD |
| 58 | 61 | 58 | 0 | 1 | AD | 82.665371 | 1.626125233 | AD |
| 69 | 76 | 74 | 1 | 1 | AD | 62.124684 | 0.347485176 | AD |
| 53 | 78 | 77 | 1 | 1 | AD | 73.01053 | −0.368801844 | NON-AD |
| 36 | 62 | 56 | 0 | 1 | ADM | 64.279215 | 2.222574634 | AD |
| 68 | 74 | 69 | 2 | 1 | ADM | 39.199015 | 1.546087454 | AD |
| 55 | 82 | 77 | 1 | 1 | ADM | 95.229315 | −1.819286352 | NON-AD |
| 78 | 75 | 72 | 1 | 1 | ADM | 46.309879 | 1.121126244 | AD |
| 47 | 67 | 65 | 1 | 1 | ADM | 59.491621 | 1.713865678 | AD |
| 63 | 83 | 80 | 1 | 1 | ADM | 51.81025 | −0.220018621 | NON-AD |
| 72 | 71 | 69 | 1 | 1 | ADM | 51.616399 | 1.468947047 | AD |
| 5 | 85 | | 0 | 0 | Control | 51.689473 | −0.495380307 | NON-AD |
| 59 | 84 | | 0 | 0 | Control | 64.100345 | −0.852459806 | NON-AD |
| 27 | 82 | | 0 | 0 | Control | 40.072426 | 0.39029862 | AD |
| 24 | 83 | | 0 | 0 | Control | 114.06898 | −2.714103481 | NON-AD |
| 62 | 61 | | 1 | 0 | Control | 119.81038 | 0.138096129 | AD |
| 35 | 70 | | 0 | 0 | Control | 50.036249 | 1.672347868 | AD |
| 70 | 83 | | 0 | 0 | Control | 177.79423 | −5.266936688 | NON-AD |
| 76 | 79 | | 1 | 0 | Control | 62.812402 | −0.100364839 | NON-AD |
| 2 | 76.3 | | 0 | 0 | Control | 54.55726 | 0.608606169 | AD |
| 1 | 76.2 | | 1 | 0 | Control | 162.72287 | −3.710498055 | NON-AD |
| 8 | 70.2 | | 0 | 0 | Control | 97.326273 | −0.250110501 | NON-AD |
| 13 | 91.6 | | 0 | 0 | Control | 46.019608 | −1.192905488 | NON-AD |
| 22 | 80.8 | | 0 | 0 | Control | 110.82108 | −2.275772576 | NON-AD |
| 52 | 82.3 | | 1 | 0 | Control | 140.55778 | −3.67717478 | NON-AD |
| 64 | 56 | 43.00 | 0 | | DNOS | 31.644344 | 4.370527582 | AD |
| 66 | 67.43 | 57.33 | 1 | | DNOS | 69.065776 | 1.270082009 | AD |
| 77 | 79 | 77 | 0 | | DNOS | 97.269799 | −1.480728141 | NON-AD |
| 74 | 72 | 65 | 1 | | possAD | 56.774929 | 1.122196334 | AD |
| 67 | 60 | 56 | 2 | | possAD | 60.104877 | 2.669998628 | AD |
| 50 | 63 | 62 | 0 | | possAD | 98.095476 | 0.727795234 | AD |
| 4 | 66 | 55 | 0 | | preAD | 0 | 4.2372 | AD |
| 26 | 86 | 81.97 | 0 | | preAD | 26.099208 | 0.389665733 | AD |
| 6 | 67 | 58.68 | 1 | | preAD | 0 | 4.0971 | AD |
| 23 | 76 | 81.54 | 0 | | preAD | 36.175497 | 1.387009603 | AD |
| 71 | 87 | 84.00 | 0 | | preAD | 54.457614 | −0.886472028 | NON-AD |
| 54 | 60 | 68.56 | 1 | | preAD | 39.202319 | 3.507355094 | AD |

TABLE 2-continued

| Bloodtest ID | Age | Age Of Onset | ApoE4* | ROC For Cutoff | Diagnosis Patent | dG1 | Variable For New DG | Dg Based On Ly Test |
|---|---|---|---|---|---|---|---|---|
| 7 | 69.8 | 70.78 | 0 |  | preAD | 0 | 3.70482 | AD |
| 51 | 83.2 | 81 | 0 |  | preAD | 72.576767 | −1.079945289 | NON-AD |
| 9 | 68.5 | 67.48 | 1 |  | preAD | 44.48544 | 2.104863289 | AD |
| 11 | 68.3 | 68.3 | 0 |  | preAD | 31.370284 | 2.658276407 | AD |
| 3 | 83.9 | 82.00 | 0 |  | preAD | 25.467302 | 0.709189896 | AD |
| 21 | 77.5 | 77.5 | 1 |  | preAD | 35.019844 | 1.223155041 | AD |
| 20 | 66.9 | 67.96 | 0 |  | preAD | 42.09647 | 2.424725428 | AD |

KEY for Table 2:
Blood Test ID: Unique anonymised identifier of the patient sample, which if necessary allows the data to be linked with other clinical data collections involving the same patients.
Age: Age of the patient at the time the test was carried out.
Age of Onset: The age when first subjective cognitive impairment has been notice by care giver or (in the case of preAD patients) by the person themselves.
ApoE4*: The number of ApoE4 alleles; derived for the ApoE genotype. The "0" category includes patients with ApoE3/3, ApoE3/2 and ApoE2/2 genotypes. The "1" category includes patients with ApoE3/4 and ApoE2/4 genotypes. The "2" category includes the patients with the ApoE4/4 genotype.
ROC for cutoff: the clinical diagnostic categories used to set the cut off point for the lymphocyte test using the logistic regression then ROC analysis. 0=Control; 1=Patients diagnosed as probably AD (by the NINCDS-ARDRA criteria (which includes the AD (pure AD) and ADM (AD mixed with other diseases such as vascular disease) categories.
Diagnosis patent: The original diagnoses (clinical based on the NINCDS criteria).
dG1: Relative lengthening of the G1 phase of the cell cycle under Rapamycin effect.
Variable for new DG: Variable calculated from the relationship of the clinical diagnosis (AD or control) and the relative lengthening of the G1 phase and the age of the patient (calculated from the logistic regression);
Dg based on Ly test: Diagnosis of the patients based on the lymphocyte test using the cut-off point established with the ROC curve.

TABLE 3

| Blood test ID | KM endpoint to at or below 27 | Age first at or below MMSE 27 | First MMSE at or below 27 | Age at test | Age Last normal | Diagnosis | DG ROC | Dg based on Ly test |
|---|---|---|---|---|---|---|---|---|
| 4 | 1 | 55.81 | 27 | 66 | 55.00 | preAD |  | AD |
| 26 | 1 | 82.99 | 26 | 86 | 81.97 | preAD |  | AD |
| 6 | 1 | 60.19 | 26 | 67 | 58.68 | preAD |  | AD |
| 23 | 0 |  |  | 76 | 81.54 | preAD |  | AD |
| 49 | 1 | 66.42 | 27 | 72 | 62.00 | AD | 1 | AD |
| 74 | 1 | 66.52 | 24 | 72 | 65.00 | possAD |  | AD |
| 64 | 1 | 56.96 | 24 | 56 | 43.00 | DNOS |  | AD |
| 33 | 1 | 55.52 | 26 | 58 | 52.00 | AD | 1 | AD |
| 36 | 1 | 58.00 | 18 | 62 | 56.00 | ADM | 1 | AD |
| 10 | 1 | 66.02 | 16 | 68 | 61.00 | AD | 1 | AD |
| 25 | 1 | 66.99 | 27 | 69 | 63.00 | AD | 1 | AD |
| 68 | 1 | 71.94 | 16 | 74 | 69.00 | ADM | 1 | AD |
| 67 | 1 | 57.95 | 27 | 60 | 56.00 | possAD |  | AD |
| 71 | 1 | 85.00 | 25 | 87 | 84.00 | preAD |  | NON-AD |
| 75 | 1 | 79.99 | 25 | 82 | 78.00 | AD | 1 | AD |
| 14 | 1 | 65.95 | 19 | 67 | 64.00 | AD | 1 | AD |
| 55 | 1 | 80.93 | 15 | 82 | 77.00 | ADM | 1 | NON-AD |
| 58 | 1 | 59.95 | 22 | 61 | 58.00 | AD | 1 | AD |
| 69 | 1 | 74.99 | 13 | 76 | 74.00 | AD | 1 | AD |
| 78 | 1 | 73.95 | 25 | 75 | 72.00 | ADM | 1 | AD |
| 77 | 1 | 77.97 | 27 | 79 | 77.00 | DNOS |  | NON-AD |
| 53 | 1 | 78.00 | 19 | 78 | 77.00 | AD | 1 | NON-AD |
| 54 | 0 |  |  | 60 | 68.56 | preAD |  | AD |
| 50 | 1 | 63.00 | 15 | 63 | 62.00 | possAD |  | AD |
| 47 | 1 | 67.00 | 22 | 67 | 65.00 | ADM | 1 | AD |
| 63 | 1 | 83.00 | 25 | 83 | 80.00 | ADM | 1 | NON-AD |
| 72 | 1 | 71.00 | 11 | 71 | 69.00 | ADM | 1 | AD |
| 7 | 0 |  |  | 69.8 | 70.78 | preAD |  | D |
| 51 | 1 | 81.84 | 27 | 83.2 | 81.00 | preAD |  | NON-AD |
| 9 | 1 | 68.50 | 27 | 68.5 | 67.48 | preAD |  | AD |
| 11 | 0 |  |  | 68.3 | 68.30 | preAD |  | AD |
| 3 | 1 | 82.90 | 26 | 83.9 | 82.00 | preAD |  | AD |
| 21 | 0 |  |  | 77.5 | 77.50 | preAD |  | AD |
| 20 | 1 | 70.13 | 27 | 66.9 | 67.96 | preAD |  | AD |

KEY for Table 3:

Blood Test ID: Unique anonymised identifier of the patient sample, which if necessary allows the data to be linked with other clinical data collections involving the same patients.

Age at test: Age of the patient at the time the test was carried out.

Age Last normal: Age of the patient when first subjective cognitive impairment has been notice by care giver or (in the case of preAD patients) by the person themselves.

Diagnosis: The original diagnoses (clinical based on the NINCDS criteria).

DG ROC: The clinical diagnostic categories used to set the cut off point for the lymphocyte test using the logistic regression then ROC analysis. 0=Control; 1=Patients diagnosed as probably AD (by the NINCDS-ARDRA criteria (which includes the AD (pure AD) and ADM (AD mixed with other diseases such as vascular disease) categories. This category is applicable to patients with the diagnosis of probable Ad (AD and ADM and above) and healthy controls, and not applicable to other patients included in the study.

Dg based on Ly test: Diagnosis of the patients based on the lymphocyte test using the cut-off point established with the ROC curve.

With reference to FIG. 2, the data is provided as an ANOVA test showing that the relative lengthening or change of the G1 phase (dG1) of the cell cycle under the effects of rapamycin is different in the different patient groups.

One-way analysis of variance (Data: dG1; Factor codes: Diagnosis patent; Sample Size: 49): Table 4: Levene's Test for Equality of Variances:

TABLE 4

| Levene's Test for Equality of Variances | |
|---|---|
| Levene Statistic | 3.736 |
| DF 1 | 5 |
| DF 2 | 43 |
| Significance Level | P = 0.007 |

Table 5—ANOVA:

TABLE 5

| ANOVA | | | |
|---|---|---|---|
| Source of variation | Sum of Squares | DF | Mean Square |
| Between groups (influence factor) | 26073.1318 | 5 | 5214.6264 |
| Within groups (other fluctuations) | 45324.4430 | 43 | 1054.0568 |
| Total | 71397.5748 | 48 | |
| F-ratio | | 4.947 | |
| Significance Level | | P = 0.001 | |

Table 6—Student-Newman-Keuls Test for All Pairwise Comparisons:

TABLE 6

| Student-Newman-Keuls Test For All Pairwise Comparisons | | | |
|---|---|---|---|
| Factor | n | Mean (dG1) | Different (P < 0.05) from factor nr |
| (1) AD | 9 | 54.1602 | |
| (2) ADM | 7 | 58.2765 | |

TABLE 6-continued

| Student-Newman-Keuls Test For All Pairwise Comparisons | | | |
|---|---|---|---|
| Factor | n | Mean (dG1) | Different (P < 0.05) from factor nr |
| (3) CONTROL | 14 | 92.3135 | (6) |
| (4) DNOS | 3 | 65.9933 | |
| (5) POSSAD | 3 | 71.6584 | |
| (6) PREAD | 13 | 31.3039 | (3) |

Figure 6:
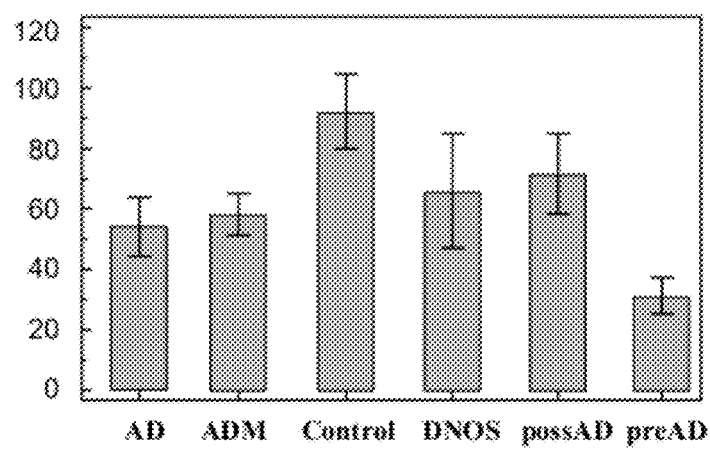
FIG. 6 illustrates graphically the mean data from the Student-Newman-Keuls test provided in Table 6 below.

The data of Table 6 is also depicted graphically in FIG. 6.

In order to determine how the relative lengthening of the G1 phase under rapamycin effect (dG1) may be used for separation of the AD patient from a Control (e.g. for the use of this variable for a diagnostic or biomarker), logistic regression is carried out. The Dependent variable is a diagnostic category or categories that are relatively certain and thus may be used as a 'gold standard' for setting the 'cut off value' for the new biomarker.

Table 7: Logistic Regression:

TABLE 7

| Logistic Regression | |
|---|---|
| Dependent Y | ROC for cutoff |
| | ROC for cutoff |
| Method | Enter |
| Sample Size | 30 |
| Cases with Y = 0 | 14 (46.67%) |
| Cases with Y = 1 | 16 (53.33%) |

Table 8: Overall Model Fit:

TABLE 8

| Overall Model Fit | |
|---|---|
| Null model −2 Log Likelihood | 41.455 |
| Full model −2 Log Likelihood | 27.870 |
| Chi-square | 13.586 |
| DF | 2 |
| Significance level | P = 0.0011 |

Table 9—Coefficients and Standard Errors

TABLE 9

| Coefficients and Standard Errors | | | |
|---|---|---|---|
| Variable | Coefficient | Std. Error | P |
| dG1 | −0.04006 | 0.01976 | 0.0427 |
| Age | −0.1401 | 0.06392 | 0.0284 |
| Constant | 13.4838 | | |

Table 10—Odds Ratios and 95% Confidence Intervals

TABLE 10

| Odds Ratios and 95% Confidence Intervals | | |
|---|---|---|
| Variable | Odds Ratio | 95% CI |
| dG1 | 0.9607 | 0.9242 to 0.9987 |
| Age | 0.8692 | 0.7669 to 0.9853 |

Table 11—Classification Table (Cut-Off Value p=0.5)

TABLE 11

| Classification Table (Cut-Off Value p = 0.5) | | | |
|---|---|---|---|
| | Predicted Group | | |
| Actual group | 0 | 1 | Percent Correct |
| Y = 0 | 10 | 4 | 71.43% |
| Y = 1 | 3 | 13 | 81.25% |
| Percent of cases correctly classified | | | 76.67% |

Table 12—ROC Curve Analysis

TABLE 12

| ROC Curve Analysis | |
|---|---|
| Area under the ROC curve (AUC) | 0.848 |
| Standard Error | 0.0717 |
| 95% Confidence Interval | 0.670 to 0.952 |

Based on the logistic regression above, we came up with a novel variable (based on the dG1 and age of the patients at the time of the test) that best relates to the diagnosis of the patients (AD or Control). The new variable ("Variable for new DG")=13.4838−(0.04006*dG1)−(0.1401*Age).

Figure 7:
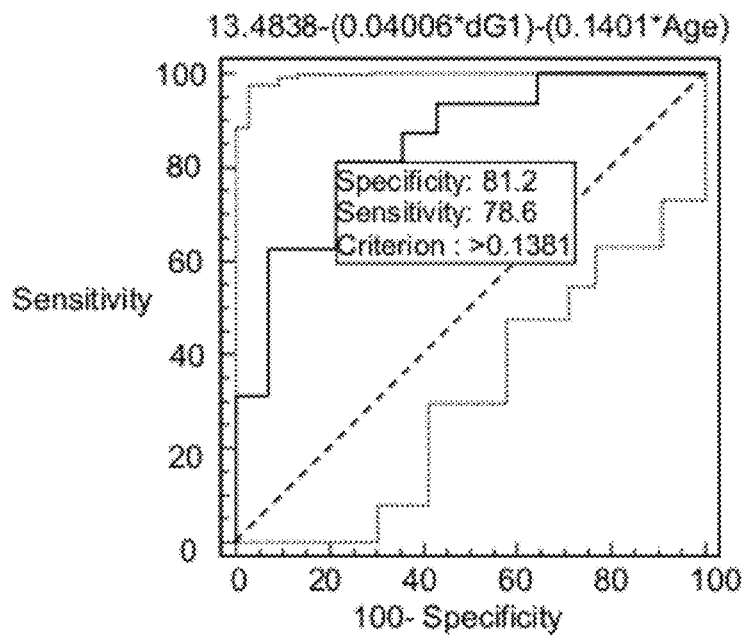
FIG. 7 shows the results of a Receiver Operating Characteristic (ROC) curve analysis to test the diagnostic performance of the variable derived from the lymphocyte test relative to the NINCDS clinical diagnostic criteria. As the variable derived from the Lymphocyte test is a continuous variable with the possibility of different cut-off point to discriminate between Control and Probable AD subjects. In the ROC curve the true positive rate (Sensitivity) is plotted in function of the false positive rate (100-Specificity) for different cut-off points. Each point on the ROC plot represents a sensitivity/specificity pair corresponding to a particular decision threshold.

ROC analysis of the new variable indicates that, based on the resulting number, the Area under the ROC curve (AUC) =84.8%. In other words, we may be about 85% certain with a prediction or likelihood of AD if a patient is randomly selected, with a standard error of about 0.0712. The 95% Confidence Interval (0.670 to 0.952) does not include the 0.5, which means that the prediction based on this variable is much better than chance. The statistical significance of the prediction is P (Area=0.5)<0.0001. The ROC curve also indicates that the best cut-off point for the new variable (in order to distinguish AD from Control) is 0.1381. Patients below this cut-off qualify as non-AD, while patients above this cut-off qualify as AD based on the lymphocyte test. At this cut-off, the sensitivity is about 81.25%, while the specificity is about 78.57%. The data in the ROC curve are represented graphically in FIG. 7.

Table 13—ROC Curve

TABLE 13

| ROC Curve Analysis | |
|---|---|
| Variable | 13.4838 − (0.04006 * dG1) − (0.1401 * Age) |
| Classification variable | ROC for cutoff |
| | ROC for cutoff |
| Sample size | 30 |
| Positive group (ROC for cutoff = 1): | 16 |
| Negative group (ROC for cutoff = 0): | 14 |
| Disease prevalence (%) | Unknown |
| Area under the ROC curve (AUC) | 0.848 |
| Standard Error[a] | 0.0712 |
| 95% Confidence Interval[b] | 0.670 to 0.952 |
| z statistic | 4.891 |
| Significance level P (Area = 0.5) | <0.0001 |

[a]DeLong et al., 1988;
[b]Binomial exact

Table 14—Criterion Values and Coordinates of the ROC Curve

TABLE 14

| Criterion Values And Coordinates Of The ROC Curve | | | | | | |
|---|---|---|---|---|---|---|
| Criterion | Sensitivity | 95% CI | Specificity | 95% CI | +LR | −LR |
| >=−5.2669 | 100.00 | 79.4-100.0 | 0.00 | 0.0-23.2 | 1.00 | |
| >−5.2669 | 100.00 | 79.4-100.0 | 7.14 | 0.2-33.9 | 1.08 | 0.00 |
| >−3.7105 | 100.00 | 79.4-100.0 | 14.29 | 1.8-42.8 | 1.17 | 0.00 |
| >−3.6772 | 100.00 | 79.4-100.0 | 21.43 | 4.7-50.8 | 1.27 | 0.00 |
| >−2.7141 | 100.00 | 79.4-100.0 | 28.57 | 8.4-58.1 | 1.40 | 0.00 |
| >−2.2758 | 100.00 | 79.4-100.0 | 35.71 | 12.8-64.9 | 1.56 | 0.00 |
| >−1.8193 | 93.75 | 69.8-99.8 | 35.71 | 12.8-64.9 | 1.46 | 0.17 |
| >−1.1929 | 93.75 | 69.8-99.8 | 42.86 | 17.7-71.1 | 1.64 | 0.15 |
| >−0.8525 | 93.75 | 69.8-99.8 | 50.00 | 23.0-77.0 | 1.87 | 0.13 |
| >−0.4954 | 93.75 | 69.8-99.8 | 57.14 | 28.9-82.3 | 2.19 | 0.11 |
| >−0.3688 | 87.50 | 61.7-98.4 | 57.14 | 28.9-82.3 | 2.04 | 0.22 |
| >−0.2501 | 87.50 | 61.7-98.4 | 64.29 | 35.1-87.2 | 2.45 | 0.19 |
| >−0.22 | 81.25 | 54.4-96.0 | 64.29 | 35.1-87.2 | 2.28 | 0.29 |
| >−0.1004 | 81.25 | 54.4-96.0 | 71.43 | 41.9-91.6 | 2.84 | 0.26 |
| >0.1381* | 81.25 | 54.4-96.0 | 78.57 | 49.2-95.3 | 3.79 | 0.24 |
| >0.2085 | 75.00 | 47.6-92.7 | 78.57 | 49.2-95.3 | 3.50 | 0.32 |
| >0.2318 | 68.75 | 41.3-89.0 | 78.57 | 49.2-95.3 | 3.21 | 0.40 |
| >0.3475 | 62.50 | 35.4-84.8 | 78.57 | 49.2-95.3 | 2.92 | 0.48 |
| >0.3903 | 62.50 | 35.4-84.8 | 85.71 | 57.2-98.2 | 4.37 | 0.44 |
| >0.6086 | 62.50 | 35.4-84.8 | 92.86 | 66.1-99.8 | 8.75 | 0.40 |
| >1.1211 | 56.25 | 29.9-80.2 | 92.86 | 66.1-99.8 | 7.88 | 0.47 |
| >1.4689 | 50.00 | 24.7-75.3 | 92.86 | 66.1-99.8 | 7.00 | 0.54 |
| >1.4774 | 43.75 | 19.8-70.1 | 92.86 | 66.1-99.8 | 6.13 | 0.61 |
| >1.5461 | 37.50 | 15.2-64.6 | 92.86 | 66.1-99.8 | 5.25 | 0.67 |
| >1.6261 | 31.25 | 11.0-58.7 | 92.86 | 66.1-99.8 | 4.38 | 0.74 |
| >1.6723 | 31.25 | 11.0-58.7 | 100.00 | 76.8-100.0 | | 0.69 |
| >1.7139 | 25.00 | 7.3-52.4 | 100.00 | 76.8-100.0 | | 0.75 |
| >2.2226 | 18.75 | 4.0-45.6 | 100.00 | 76.8-100.0 | | 0.81 |
| >2.7352 | 12.50 | 1.6-38.3 | 100.00 | 76.8-100.0 | | 0.88 |
| >3.2095 | 6.25 | 0.2-30.2 | 100.00 | 76.8-100.0 | | 0.94 |
| >3.957 | 0.00 | 0.0-20.6 | 100.00 | 76.8-100.0 | | 1.00 |

To show the range and distribution of this new diagnostic variable in the whole patient cohort we have performed ANOVA test. This indicates that The AD and ADM patients are significantly different from the Control group, while the preAD (also referred to as the "MCI") patients are also significantly different from the Control group. The DNOS and PossAD groups have relatively small patient numbers and thus exhibit more variability.

One-way analysis of variance (Data: Variable for new DG; Factor codes: Diagnosis patent; Sample Size 49):

Table 15—Levene's Test for Equality of Variances

TABLE 15

| Levene's Test for Equality of Variances | |
|---|---|
| Levene Statistic | 0.873 |
| DF 1 | 5 |
| DF 2 | 43 |
| Significance Level | P = 0.507 |

Table 16—ANOVA

TABLE 16

| ANOVA | | | |
|---|---|---|---|
| Source of variation | Sum of Squares | DF | Mean Square |
| Between groups (influence factor) | 81.4922 | 5 | 16.2984 |

TABLE 16-continued

ANOVA

| Source of variation | Sum of Squares | DF | Mean Square |
|---|---|---|---|
| Within groups (other fluctuations) | 138.7063 | 43 | 3.2257 |
| Total | 220.1985 | 48 | |
| F-ratio | | 5.053 | |
| Significance Level | | $P = 0.001$ | |

Table 17—Student-Newman-Keuls Test for All Pairwise Comparisons

TABLE 17

Student-Newman-Keuls Test For All Pairwise Comparisons

| Factor | n | Mean (dG1) | Different ($P < 0.05$) from factor nr |
|---|---|---|---|
| (1) AD | 9 | 1.4916 | (3) |
| (2) ADM | 7 | 0.8619 | (3) |
| (3) CONTROL | 14 | −1.2662 | (1)(2)(6) |
| (4) DNOS | 3 | 1.3866 | |
| (5) POSSAD | 3 | 1.5067 | |
| (6) PREAD | 13 | 1.8828 | (3) |

Figure 8:
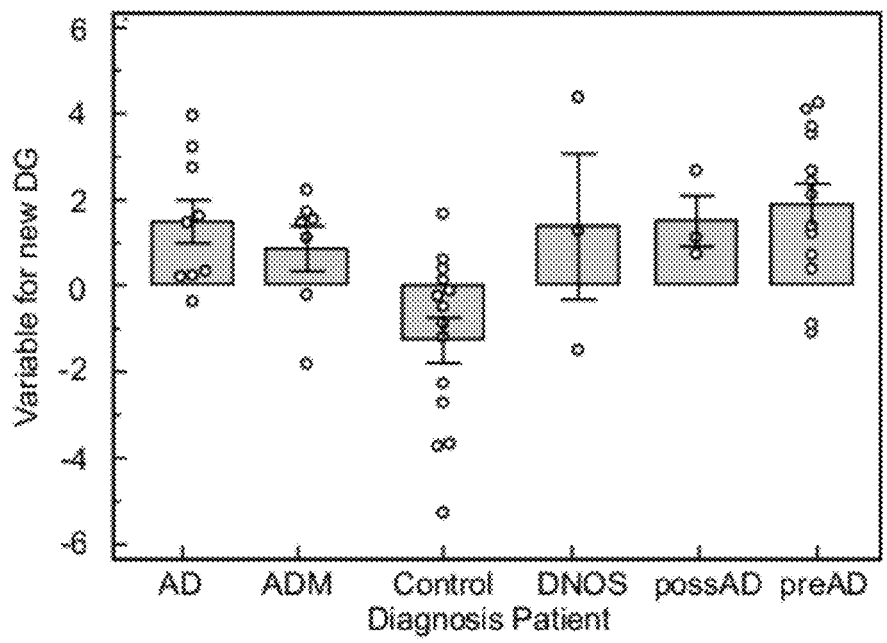
FIG. 8 illustrates graphically the mean data from the Student-Newman-Keuls test provided in Table 17 below.

The data of Table 17 is represented graphically in FIG. 8.

Figure 9:
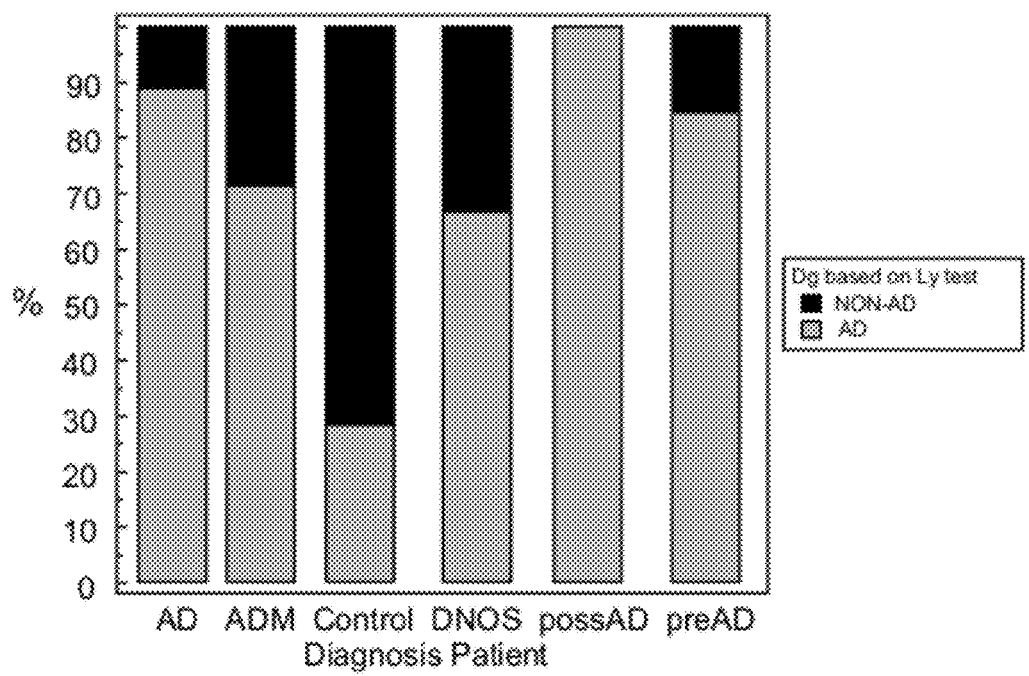
FIG. 9 illustrates graphically the data presented in Table 18 below, showing the relationship between the clinical diagnosis (Diagnosis patent) and the diagnosis established based on the lymphocyte test (Dg based on Ly test).

The relationship between the clinical diagnosis (Diagnosis patent) and the diagnosis established based on the lymphocyte test (Dg based on Ly test) is shown below, and depicted graphically in FIG. 9.

Table 18—Frequency Table & Chi-Square Test:

TABLE 18

Frequency Table & Chi-Square Test

| Codes Y (Dg Based on Ly Test) | Codes X (Diagnosis of Patient) | | | | | | |
|---|---|---|---|---|---|---|---|
| | AD | ADM | CONTROL | DNOS | POSSAD | PREAD | |
| AD | 8 | 5 | 4 | 2 | 3 | 11 | 33 (67.3%) |
| Non-AD | 1 | 2 | 10 | 1 | 0 | 2 | 16 (32.7%) |
| | 9 (18.4%) | 7 (14.3%) | 14 (28.6%) | 3 (6.1%) | 3 (6.1%) | 13 (26.5%) | 49 |
| Chi-square | | | 14.742 | | | | |
| DF | | | 5 | | | | |
| Significance level | | | $P = 0.0115$ | | | | |
| Contingency coefficient | | | 0.481 | | | | |

We also analyzed the age of onset in relation to the lymphocyte test outcome in the preAD and AD patient groups. Both analysis indicate that the Ly test indicative of AD is associated with an earlier age of onset in both the preAD patients and the patients diagnosed with probable AD by the NINCDS criteria.

One-way analysis of variance (Data: Age of Onset; Factor code: Dg Based on Ly test; Select: Diagnosis patent="preAD"; Sample size: 13):

Table 19—Levene's Test for Equality of Variances

TABLE 19

| Levene's Test for Equality of Variances | |
|---|---|
| Levene Statistic | 2.210 |
| DF 1 | 1 |
| DF 2 | 11 |
| Significance Level | $P = 0.165$ |

Table 20—ANOVA

TABLE 20

ANOVA

| Source of variation | Sum of Squares | DF | Mean Square |
|---|---|---|---|
| Between groups (influence factor) | 228.0936 | 1 | 228.0936 |
| Within groups (other fluctuations) | 841.6781 | 11 | 76.5162 |
| Total | 1069.7717 | 12 | |
| F-ratio | | 2.981 | |
| Significance Level | | $P = 0.112$ | |

| Factor | n | Mean |
|---|---|---|
| (1) AD | 11 | 70.8904 |
| (2) Non-AD | 2 | 82.5000 |

Figure 10:
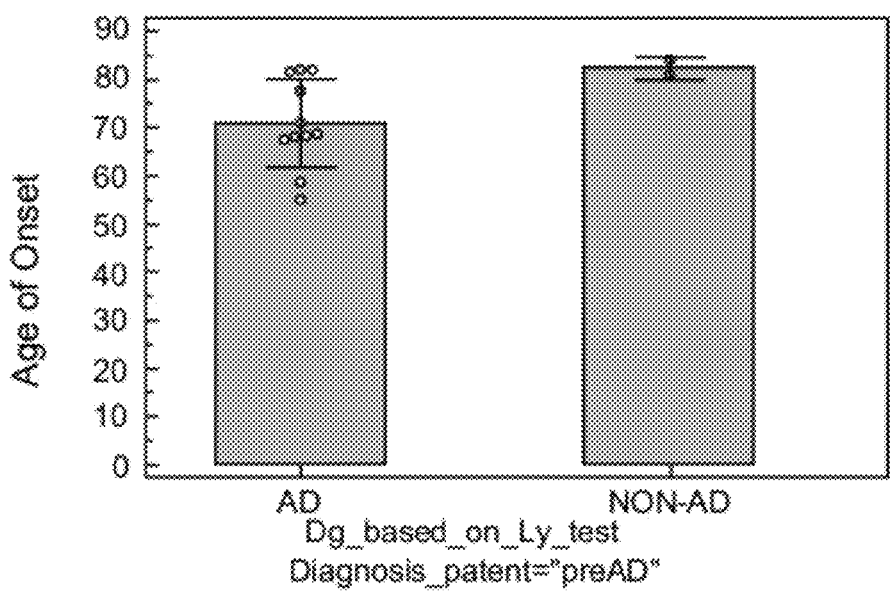
FIG. 10 illustrates graphically the mean results of the data presented in Table 20 below.

The mean results of Table 20 are depicted graphically in FIG. 10.

One-way analysis of variance (Data: Age of Onset; Factor Codes: Dg based on Ly test; Select: ROC for cutoff=1; Sample size: 16):

Table 21—Levene's Test for Equality of Variances

TABLE 21

| Levene's Test for Equality of Variances | |
|---|---|
| Levene Statistic | 3.173 |
| DF 1 | 1 |
| DF 2 | 14 |
| Significance Level | $P = 0.097$ |

Table 22—ANOVA

TABLE 22

ANOVA

| Source of variation | Sum of Squares | DF | Mean Square |
|---|---|---|---|
| Between groups (influence factor) | 421.7452 | 1 | 421.7452 |
| Within groups (other fluctuations) | 665.6923 | 14 | 47.5495 |
| Total | 1087.4375 | 15 | |
| F-ratio | | 8.870 | |
| Significance Level | | P = 0.010 | |

Table 23—Student-Newman-Keuls Test for All Pairwise Comparisons

TABLE 23

Student-Newman-Keuls Test For All Pairwise Comparisons

| | Factor | n | Mean (dG1) | Different (P < 0.05) from factor nr |
|---|---|---|---|---|
| (1) | AD | 13 | 64.8462 | (2) |
| (2) | Non-AD | 3 | 78.0000 | (1) |

Figure 11:
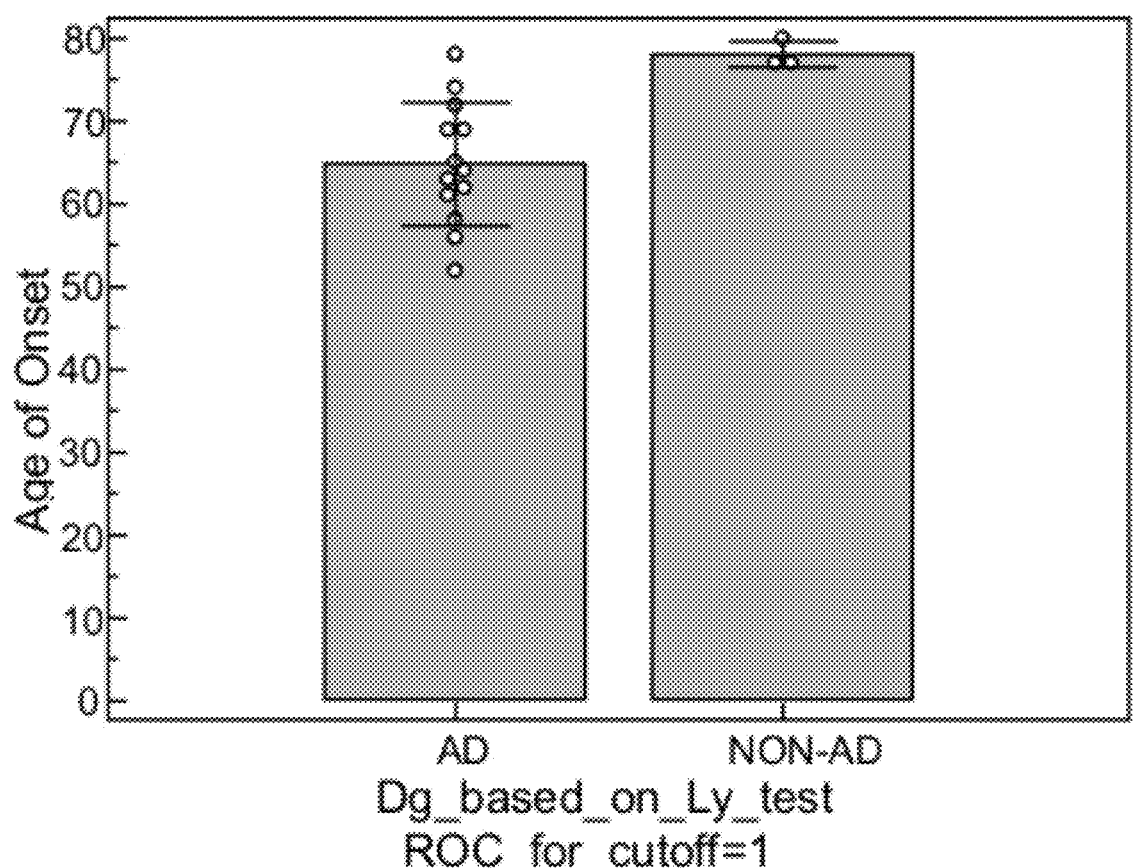
FIG. 11 illustrates graphically the mean results from the Student-Newman-Keuls test presented in Table 23 below.

The mean results of Table 23 are depicted graphically in FIG. 11.

Figure 12:
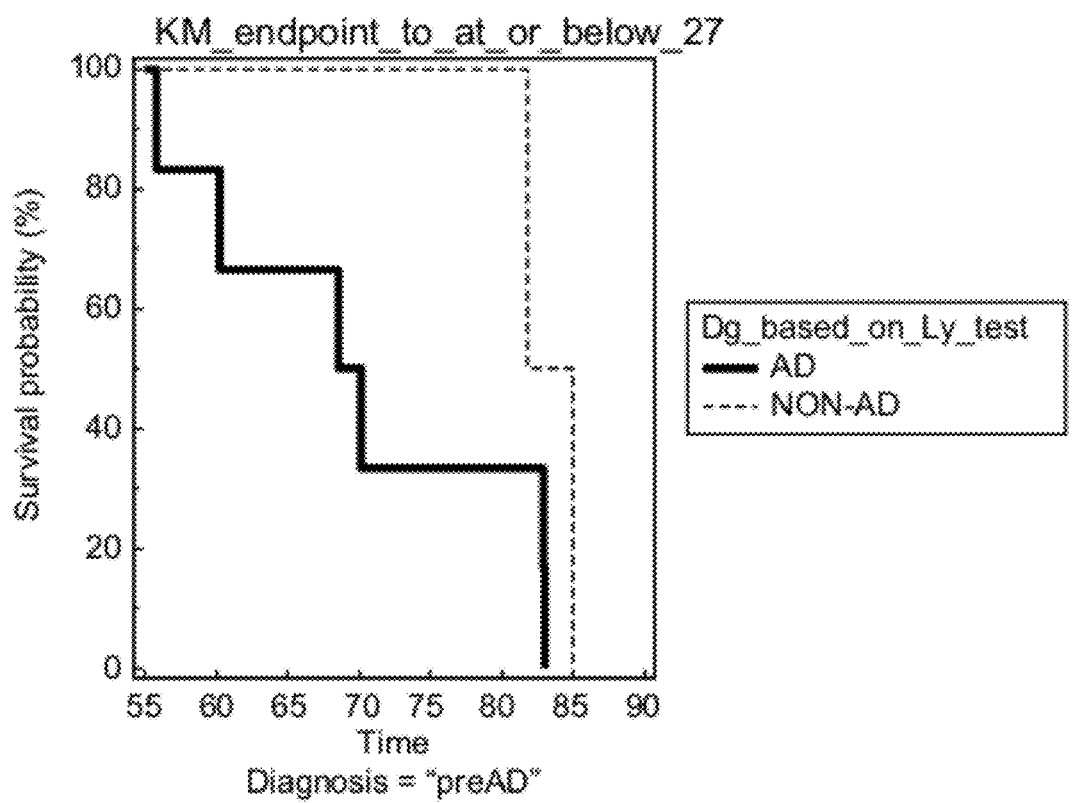
FIG. 12 illustrates graphically the survival proportion data for AD and NON-AD patients presented in Table 24 below.

In a subset of patients, detailed yearly longitudinal follow up was available and a relatively precise time could be pinpointed as to when the preAD patient showed overt cognitive deficit, as measured by classical cognitive tests (MMSE drops to or below 27 points). The KM survival analysis below indicates that preAD patients who show AD-type test results on the lymphocyte test show overt cognitive deficit significantly earlier that those who have lymphocyte test results indicative of non-AD. The data is also illustrated graphically in FIG. 12.

Table 24—Kaplan-Meier Survival Curve:

TABLE 24

Kaplan-Meier Survival Curve

| Survival Time | Age first at or below MMSE 27 |
| Endpoint | KM endpoint to at or below 27 |
| Factor Codes | Dg based on Ly test |
| Select | Diagnosis = "preAD" |

| Factors | | |
|---|---|---|
| | AD | Non-AD |
| Sample Size | 6 | 2 |
| Median Survival | 69.3151 | 83.4205 |

| Survival Time | Survival Proportion | Standard Error | Survival Proportion | Standard Error |
|---|---|---|---|---|
| 55.8055 | 0.833 | 0.152 | — | — |
| 60.1918 | 0.667 | 0.192 | — | — |
| 68.5 | 0.500 | 0.204 | — | — |
| 70.1301 | 0.333 | 0.192 | — | — |
| 81.8384 | — | — | 0.500 | 0.354 |
| 82.9027 | 0.167 | 0.152 | — | — |
| 82.9863 | 0.000 | 0.000 | — | — |
| 85.0027 | — | — | 0.000 | 0.000 |

| Comparison of Survival Curves (Logrank Test) | | |
|---|---|---|
| Endpoint: Observed n | 6.0 | 2.0 |
| Expected n | 4.4 | 3.6 |
| Chi-square | 1.6292 | |
| DF | 1 | |
| Significance | P = 0.2018 | |

Table 25—Hazard Ratio

TABLE 25

Hazard Ratio

| Hazard Ratio | 0.4069 |
| 95% CI | 0.1011 to 1.6383 |

An alternative analytical approach to the data presented in the KM curves is provided below:

One-way analysis of variance (Data: Age first at or below MMSE 27; Factor codes: Dg based on Ly test; Select: Diagnosis="preAD"; Sample size: 8):

Table 26—Levene's Test for Equality of Variances

TABLE 26

Levene's Test for Equality of Variances

| Levene Statistic | 2.293 |
| DF 1 | 1 |
| DF 2 | 6 |
| Significance Level | P = 0.181 |

Table 27—ANOVA

TABLE 27

ANOVA

| Source of variation | Sum of Squares | DF | Mean Square |
|---|---|---|---|
| Between groups (influence factor) | 266.7123 | 1 | 266.7123 |
| Within groups (other fluctuations) | 640.0394 | 6 | 106.6732 |
| Total | 906.7518 | 7 | |
| F-ratio | | 2.500 | |
| Significance Level | | P = 0.165 | |

| Factor | n | Mean |
|---|---|---|
| (1) AD | 6 | 70.0861 |
| (2) Non-AD | 2 | 83.4205 |

Figure 13:
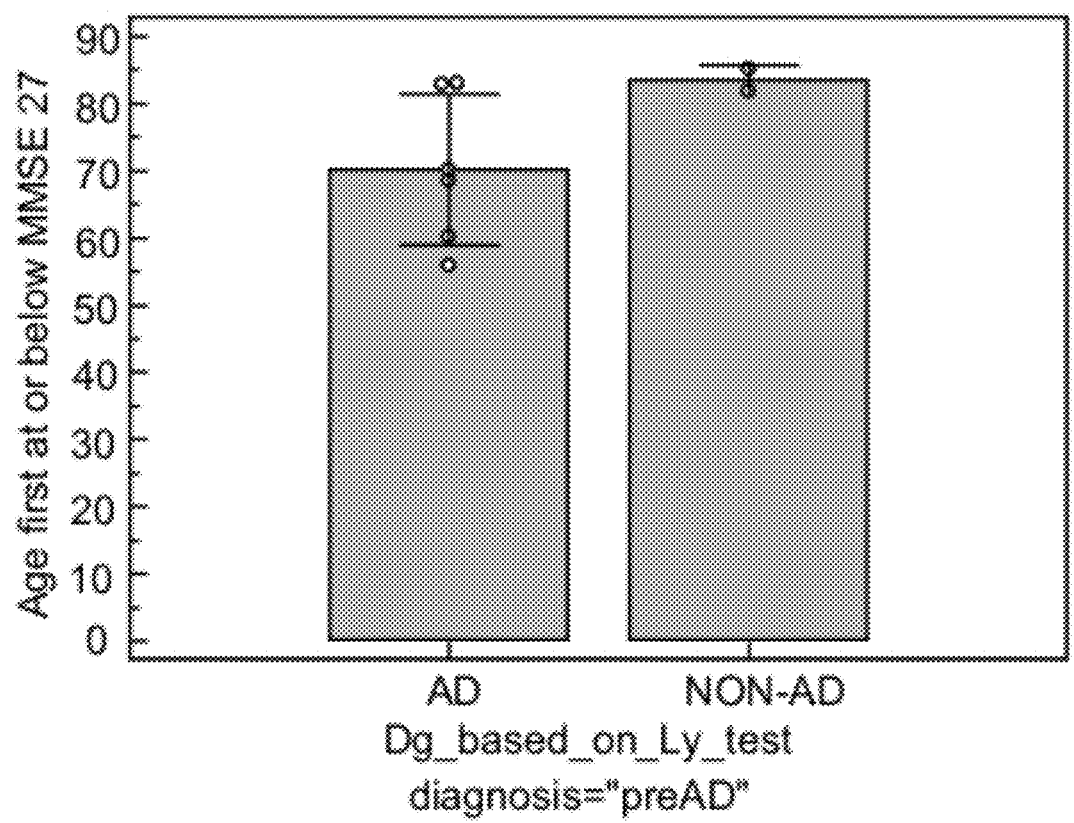
FIG. 13 illustrates graphically the mean results of the data presented in Table 27 below.

The resulting mean data is depicted graphically in FIG. 13.

The ApoE genotype of the patients became available for these patients. For comparison, we performed the analysis of the same patient group for the value of the ApoE4 genotype (a known and generally accepted risk factor for AD) for clinical diagnosis and risk prediction.

Logistic regression and follow-up ROC curve analysis (below) shows that although the ApoE4 status is a risk factor for AD its predictive value is poorer than that of the lymphocyte test. (Sensitivity 62.5% and specificity 71.43%).

Table 28—Logistic Regression:

TABLE 28

| Linear Regression | |
| --- | --- |
| Dependent Y | ROC for Cutoff |
| Method | Backward |
| Enter Variable if P< | 0.05 |
| Remove Variable if P> | 0.1 |
| Sample Size | 30 |
| Cases with Y = 0 | 14 (46.67%) |
| Cases with Y = 1 | 16 (53.33%) |

Table 29: Overall Model Fit:

TABLE 29

| Overall Model Fit | |
| --- | --- |
| Null model −2 Log Likelihood | 41.455 |
| Full model −2 Log Likelihood | 37.426 |
| Chi-square | 4.030 |
| DF | 1 |
| Significance level | P = 0.0447 |

Table 30—Coefficients and Standard Errors

TABLE 30

| Coefficients and Standard Errors | | | |
| --- | --- | --- | --- |
| Variable | Coefficient | Std. Error | P |
| ApoE4 | 1.4135 | 0.7517 | 0.0600 |
| Constant | −0.5354 | | |

Table 31—Odds Ratios and 95% Confidence Intervals

TABLE 31

| Odds Ratios and 95% Confidence Intervals | | |
| --- | --- | --- |
| Variable | Odds Ratio | 95% CI |
| ApoE4 | 4.1104 | 0.9420 to 17.9358 |

Table 32—Classification Table (Cut-Off Value p=0.5)

TABLE 32

| Classification Table (Cut-Off Value p = 0.5) | | | |
| --- | --- | --- | --- |
| | Predicted Group | | |
| Actual group | 0 | 1 | Percent Correct |
| Y = 0 | 10 | 4 | 71.43% |
| Y = 1 | 6 | 10 | 62.50% |
| Percent of cases correctly classified | | | 66.67% |

Table 33—ROC Curve Analysis

TABLE 33

| ROC Curve Analysis | |
| --- | --- |
| Area under the ROC curve (AUC) | 0.679 |
| Standard Error | 0.0982 |
| 95% Confidence Interval | 0.484 to 0.836 |

Table 34—ROC Curve

TABLE 34

| ROC Curve Analysis | |
| --- | --- |
| Variable | 1.4135*ApoE4-0.5354 |
| Classification variable | ROC for cutoff |
| Sample size | 30 |
| Positive group (ROC for cutoff = 1): | 16 |
| Negative group (ROC for cutoff = 0): | 14 |
| Disease prevalence (%) | Unknown |
| Area under the ROC curve (AUC) | 0.679 |
| Standard Error[a] | 0.0875 |
| 95% Confidence Interval[b] | 0.484 to 0.836 |
| z statistic | 2.041 |
| Significance level P (Area = 0.5) | 0.0413 |

[a] DeLong et al., 1988;
[b] Binomial exact

Table 35—Criterion Values and Coordinates of the ROC Curve

TABLE 35

| Criterion Values And Coordinates Of The ROC Curve | | | | | | |
| --- | --- | --- | --- | --- | --- | --- |
| Criterion | Sensitivity | 95% CI | Specificity | 95% CI | +LR | −LR |
| >=−0.5354 | 100.00 | 79.4-100.0 | 0.00 | 0.0-23.2 | 1.00 | |
| >−0.5354* | 62.50 | 35.4-84.8 | 71.43 | 41.9-91.6 | 2.19 | 0.53 |
| >0.8781 | 6.25 | 0.2-30.2 | 100.00 | 76.8-100.0 | | 0.94 |
| >2.2916 | 0.00 | 0.0-20.6 | 100.00 | 76.8-100.0 | | 1.00 |

Figure 14:
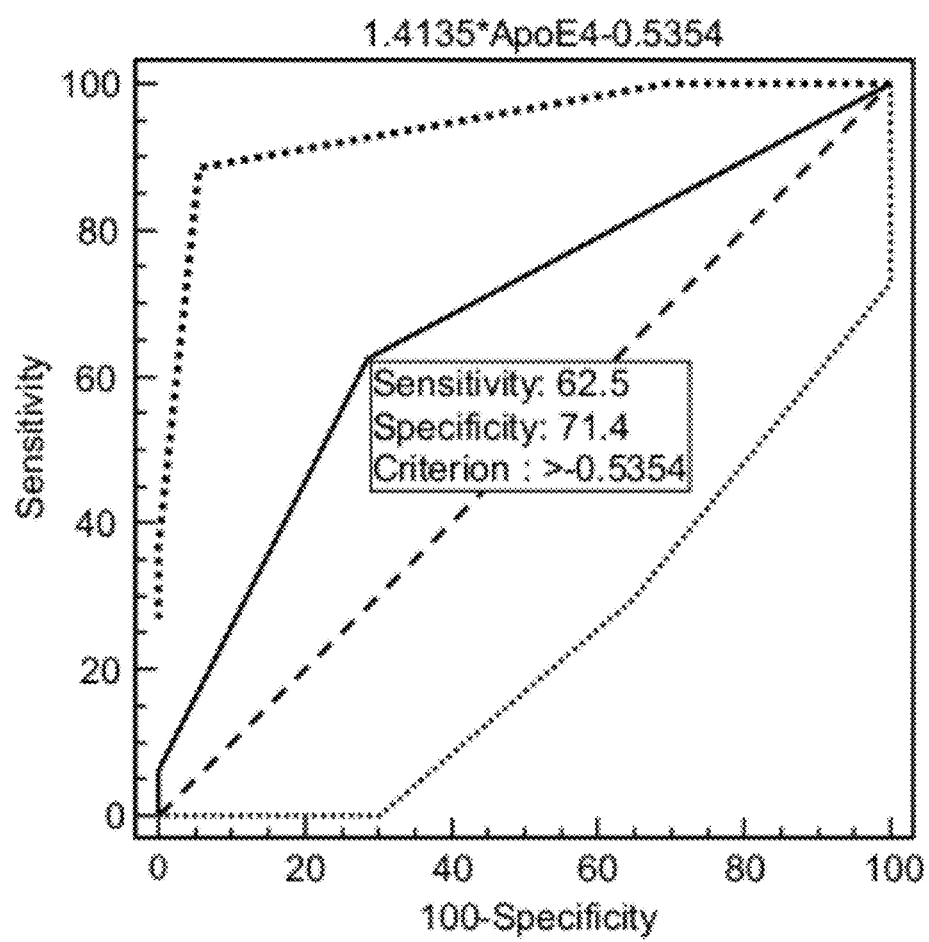
FIG. 14 shows the results of a Receiver Operating Characteristic (ROC) curve analysis to test the diagnostic performance of the ApoE genotyping relative to the NINCDS clinical diagnostic criteria. As the variable derived from the ApoE genotype is a continuous variable with the possibility of different cut-off point to discriminate between Control and Probable AD subjects. In the ROC curve the true positive rate (Sensitivity) is plotted in function of the false positive rate (100-Specificity) for different cut-off points. Each point on the ROC plot represents a sensitivity/specificity pair corresponding to a particular decision threshold.

The data of Table 35 is also depicted graphically in FIG. 14.

The distribution of the ApoE4 status in the different patient groups included in the study was analyzed by Chi square test.

Table 36—Frequency Table & Chi-Square Test:

TABLE 36

Frequency Table & Chi-Square Test

| Codes Y (ApoE4) | Codes X (Diagnosis of Patient) | | | | | | |
|---|---|---|---|---|---|---|---|
| | AD | ADM | CONTROL | DNOS | POSSAD | PREAD | |
| 0 | 5 | 1 | 10 | 2 | 1 | 9 | 28 (57.1%) |
| 1 | 4 | 5 | 4 | 1 | 1 | 4 | 19 (38.8%) |
| 2 | 0 | 1 | 0 | 0 | 1 | 0 | 2 (4.1%) |
| | 9 (18.4%) | 7 (14.3%) | 14 (28.6%) | 3 (6.1%) | 3 (6.1%) | 13 (26.5%) | 49 |
| Chi-square | | | 15.734 | | | | |
| DF | | | 10 | | | | |
| Significance level | | | P = 0.1075 | | | | |
| Contingency coefficient | | | 0.493 | | | | |

Figure 15:
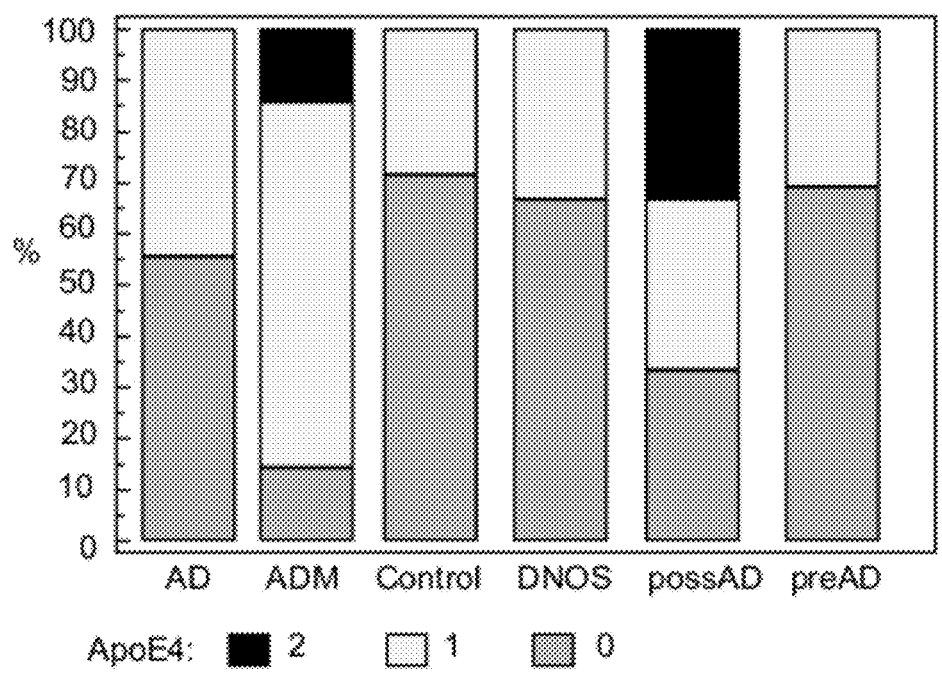
FIG. 15 illustrates graphically the data presented in Table 36 below, showing the data as percentages in a frequency chart in 100% stacked column format.

The data from Table 36 is represented graphically in FIG. 15.

The analysis also indicates that the ApoE4 status did not influence the outcome of the lymphocyte test.

One-way analysis of variance (Data: dG1; Factor codes: ApoE4; Sample size: 49):

Table 37—Levene's Test for Equality of Variances:

TABLE 37

Levene's Test for Equality of Variances

| | |
|---|---|
| Levene Statistic | 0.510 |
| DF 1 | 2 |
| DF 2 | 46 |
| Significance Level | P = 0.604 |

Table 38—ANOVA

TABLE 38

ANOVA

| Source of variation | Sum of Squares | DF | Mean Square |
|---|---|---|---|
| Between groups (influence factor) | 327.0231 | 2 | 163.5115 |
| Within groups (other fluctuations) | 71070.5517 | 46 | 1545.0120 |
| Total | 71397.5748 | 48 | |
| F-ratio | | 0.106 | |
| Significance Level | | P = 0.900 | |

| Factor | n | Mean |
|---|---|---|
| (1) 0 | 28 | 61.1186 |
| (2) 1 | 19 | 63.0025 |
| (3) 2 | 2 | 49.6519 |

Figure 16:
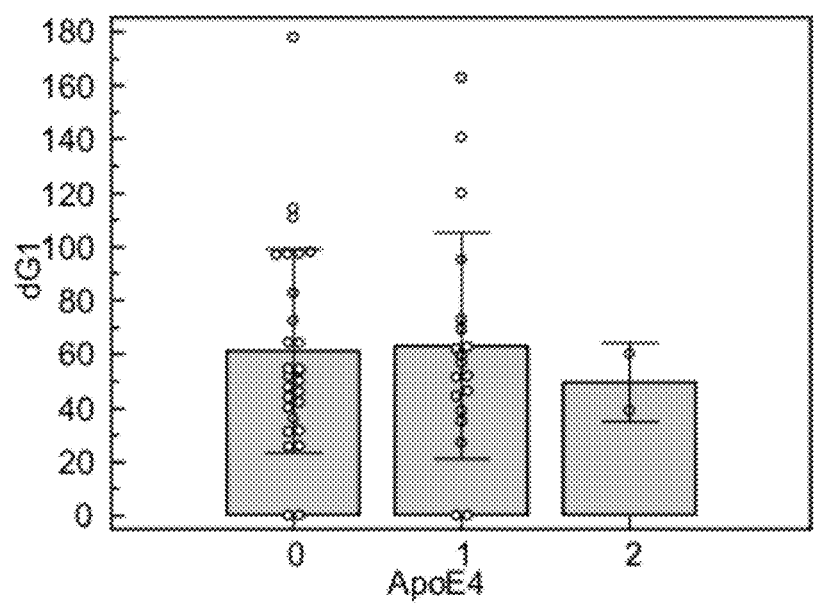
FIG. 16 illustrates graphically the mean results presented in Table 38 below.

The mean data of Table 38 is depicted graphically in FIG. 16.

Table 39—Frequency Table & Chi-Square Test:

TABLE 39

Frequency Table & Chi-Square Test

| Codes Y (ApoE4) | Codes X (Dg Based on Ly Test) | | |
|---|---|---|---|
| | AD | Non-AD | |
| 0 | 18 | 10 | 28 (57.1%) |
| 1 | 13 | 6 | 19 (38.8%) |
| 2 | 2 | 0 | 2 (4.1%) |
| | 33 (67.3%) | 16 (32.7%) | 49 |
| Chi Squared | | 1.099 | |
| DF | | 2 | |
| Significance Level | | P = 0.5772 | |
| Chi Squared Test For Trend | | | |
| Chi Squared (Trend) | | 0.640 | |
| DF | | 1 | |
| Significance Level | | P = 0.4237 | |

Figure 17:
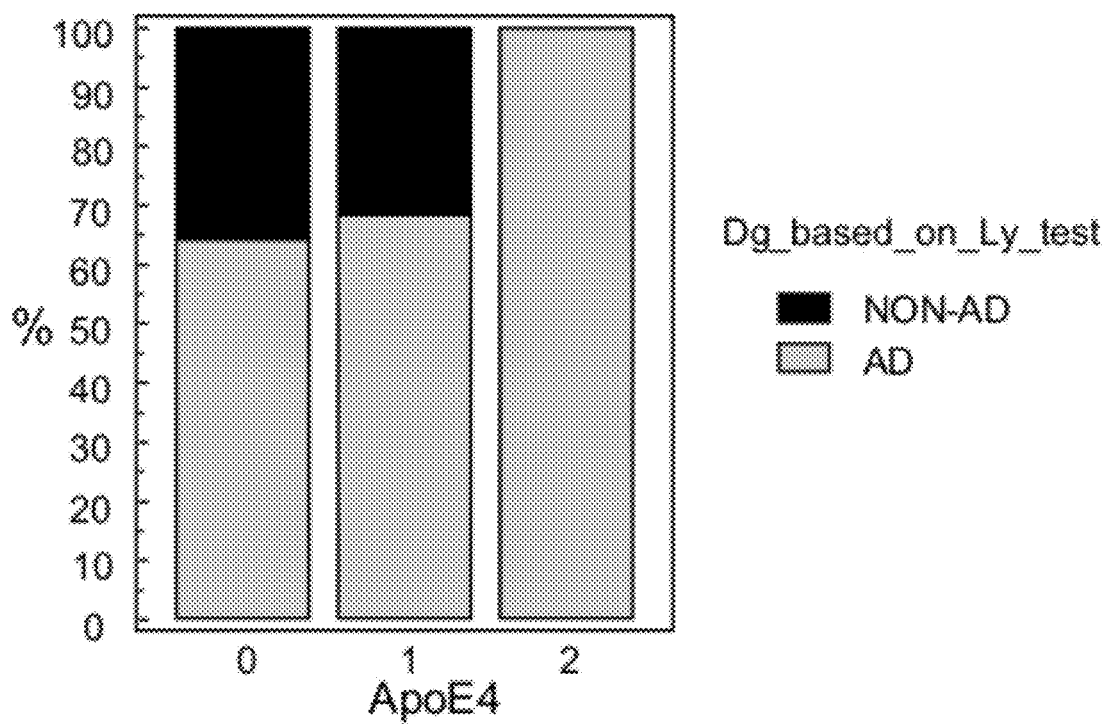
FIG. 17 illustrates graphically the data presented in Table 39 below, showing the data as percentages in a frequency chart in 100% stacked column format.

The data from Table 39 is represented graphically in FIG. 17.

Discussion

In this study the effects of a specific G1 inhibitor (rapamycin) (16, 19) on the length of the G1 phase in lymphocytes were analyzed using BrdU incorporation assay and FACS analysis. The reduction of cell numbers in the cultures following rapamycin treatment was also assessed. In a second approach, G1 inhibition was induced by oxidative stress and the reduction of cell numbers in the culture system measured.

The presented data is analyzed to provide an ROC curve, which demonstrates the clinical usefulness of the test in identifying patients correctly (as AD or non-AD). The test identifies the MCI patients who have an earlier age of onset of overt cognitive deficit measureable by cognitive tests (MMSE or other). Further, the test identifies AD patients who have an earlier age of onset of cognitive problems. The lymphocyte test is a better predictor of AD risk than the ApoE genotype.

The tests reported herein were performed on patients who did not have any blood malignancy and had not received treatment for any cancer. In particular, patients having the following conditions were excluded from the tests: any active malignancy or ongoing treatment for cancer; active viral or bacterial infection; active chronic treatment with anti-inflammatory drugs at anti-inflammatory doses (e.g. a relatively low dose aspirin for the prevention of MI was not regarded as "anti-inflammatory" treatment).

The results of the first set of experiments indicate that G1 inhibitor-induced cell cycle arrest, as indicated by the lengthening of the G1 phase of the cell cycle, is significantly less effective in patients suffering from Alzheimer's disease than in control individuals. It is also apparent that these changes appear early, at the stage when the patients are not yet clinically demented but show signs of specific rapid memory loss, known to be the first explicit sign of dementia.

The rapamycin induced G1 block depends on the expression and activity of the p27kip1 CDKI that inhibits the activity of the CyclinE/cdk2 complex (16, 19). Therefore the relative lengthening of the G1 phase under the influence of rapamycin, will depend upon the expression/activity of this CDKI (19). The fact that this relative lengthening of G1 is significantly lower in Alzheimer's disease patient than in healthy elderly individuals would support the hypothesis that a G1/S checkpoint failure in neurons might be accompanied by similar cell cycle control damage in other cell types in these patients. It is also apparent that the failure in cell cycle control is detectable in peripheral cells well before the signs of fully developed dementia appear. This makes it possible that an assay based on the mitogenic stimulation of peripheral lymphocytes followed by an attempted G1/S transition block could be used for the early detection of patients who may be at risk for developing AD-type brain pathology later.

The differences in cell numbers induced by $H_2O_2$ were significantly different in the patient groups indicating that lymphocytes from control subjects have a more pronounced response to oxidative stress. Treatment with 120 mM $H_2O_2$ has been shown to induce a reversible and temporary cell cycle arrest at the G1/S transition point (6) to allow time for DNA damage-repair. The results indicate that this mechanism is not fully efficient in Alzheimer's disease patients. This inadequate response to oxidative stress is also present in subjects suffering from preclinical AD. The altered response to oxidative stress may also be a reflection of more substantial pre-existing DNA damage in the AD patients (11). However, this possibility is excluded by the fact that doxorubicin-induced DNA damage, inducing a G2/M arrest rather than a G1 arrest, is not different in the patient groups. The results of this study are therefore interpreted as indicating a specific failure in the regulation of the G1/S transition point.

In summary, the results of this study indicate that the response of activated lymphocytes to G1 inhibition is significantly altered in Alzheimer's disease sufferers. In addition these alterations appear early before the onset of a fully developed dementia syndrome identifying subjects who are likely to develop Alzheimer' disease later. The results indicate that a diagnostic test relying on the detection of the integrity of the G1/S transition checkpoint may allow the identification of subjects who are at risk from developing AD later. The advantage of this diagnostic procedure would lie in its ability to identify this group, opening the possibility of preventive intervention for these people.

The protocols described under Example 1 for separation and culture of lymphocytes, induction of cell division, induction of cell cycle arrest by either treatment with a cell division inhibitor or $H_2O_2$-induced hypoxia, BrdU incorporation/FACS analysis and MTT survival assay, or minor adaptations thereof, may all be used diagnostically to test for the presence of a regulatory defect at the G1/S transition.

Example 2

Identification of Single Nucleotide Polymorphisms in p21cip and p57

Methods

The exon 2 of p21cip was amplified from genomic DNA (extracted from brain or blood) using 5'-CGGGATCCG-GCGCCATGTCAGAACCGGC-3' (SEQ ID NO: 1) and 5'-CCAGACAGGTCAGCCCTTGG-3' (SEQ ID NO: 2) primers. PCR amplification was carried out in a final volume of 50 µl using 1.25 units of Taq DNA polymerase, 1.5 mM $MgCl_2$, 5% Gelatine, 200 µM of each dNTP in PCR buffer (75 mM Tris-HCl, pH 8.8, 20 mM $(NH_4)_2SO_4$ and 0.01% Tween). The hot start (95° C. for 5 min) was followed by 30 cycles of 95° C. 1 min, 65° C. 1 min, 72° C. 1 min.

The first segment of exon 2 of p57 (exon 2Ap57) was amplified from genomic DNA (extracted from brain or blood) using 5'-GGCCATGTCCGACGCGTC-3' (SEQ ID NO: 3) and 5'-AGGCGGCAGCGCCCCACCTG-3' (SEQ ID NO: 4) primers. PCR amplification was carried out in a final volume of 50 µl using 1.25 units of Taq DNA polymerase, 1.5 mM $MgCl_2$, 10% DMSO, 200 µM of each dNTP in PCR buffer (75 mM Tris-HCl, pH 8.8, 20 mM $(NH_4)_2SO_4$ and 0.01% Tween). The hot start (95° C. for 5 min) was followed by 30 cycles of 95° C. 30 s, 52° C. 30 s, 72° C. 30 s.

The second segment of exon 2 of p57 (exon 2Bp57) was amplified from genomic DNA (extracted from brain or blood) using 5'-ATTACGACTTCCAGCAGGACATG-3' (SEQ ID NO: 5) and 5'-CTGGAGCCAGGACCGGGACTG-3' (SEQ ID NO: 6) primers. PCR amplification was carried out in a final volume of 50 µl using 1.25 units of Taq DNA polymerase, 1.5 mM $MgCl_2$, 200 µM of each dNTP in PCR buffer (75 mM Tris-HCl, pH 8.8, 20 mM $(NH_4)_2SO_4$ and 0.01% Tween). The hot start (95° C. for 5 min) was followed by 30 cycles of 95° C. 30 s, 53° C. 30 s, 72° C. 30 s.

For initial screening the 4 µl PCR product was added to 16 µl of denaturation solution (95% deionized formamide, 10 mM NaOH, 0.01% bromophenol blue, and 0.01% xylene cyanol FF) corresponding to 20 µl for gel loading. The mixture was incubated for 5 min at 95° C. and applied to a metaphor agarose gel (2% for exon 2 p21, and 3% for exon 2A p57 and exon2B p57) containing 1:10000 Gelstar. The electrophoresis apparatus was maintained in a standard refrigerator at a constant temperature of 4° C. Electrophoresis was carried out using 1×TBE (45 mM Tris-borate/1 mM EDTA) at 5 V/cm for 2 hours. SSCP patterns appearing on the gel were detected by UV light.

Results

Figure 19:
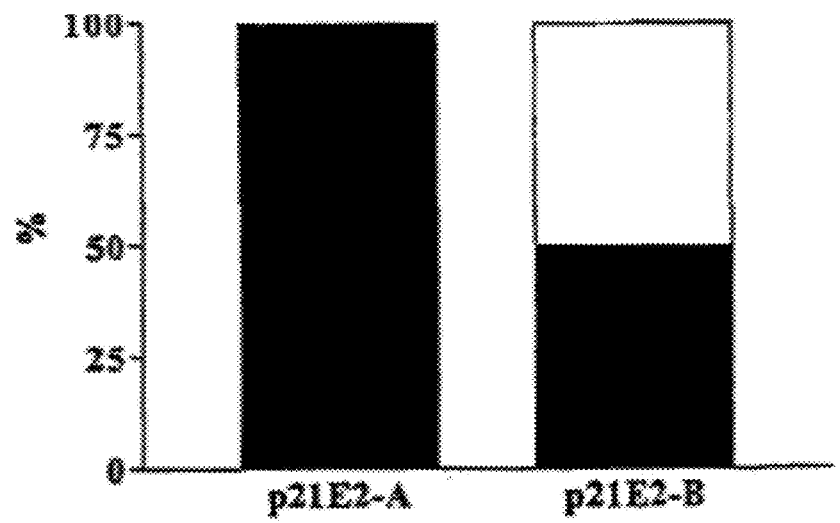
FIG. 19 illustrates the relationship between p21 variants A and B and cyclin B expression in the brain. White bar indicates the percent of patients where cyclin B was NOT expressed in neurones. Black bars indicate the percent of patients where cyclin B was expressed in neuronal nuclei.
Figure 20:
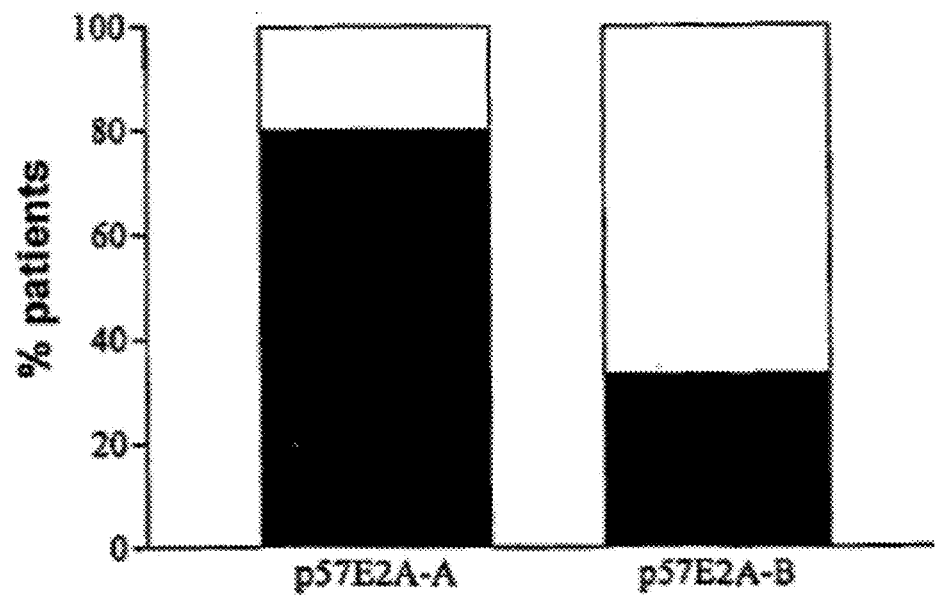
FIG. 20 illustrates the relationship between p57 exon 2A variants A and B and cyclin expression in the brain in patients with normal p21 (variant B). White bar indicates the percent of patients where cyclin B was NOT expressed in neurones. Black bars indicate the percent of patients where cyclin B was expressed in neuronal nuclei.

Polymorphisms were found on the exon 2 of the p21 cip and exon 2 of the p57 kip2 genes (FIG. 18). The polymorphism detected on the exon 2 of p21cip (variant A) was significantly associated with cell cycle de-regulation in neurones (FIG. 19), i.e. the progression of the cell cycle through the G1/S transition into the G2 phase, as indicated by cyclin B positivity. In patients with normal p21 cip (variant B) the polymorphism on p57 exon 2A is associated with cyclin B positivity (FIG. 20), indicating progression of the cell cycle through the G1/S transition into the G2 phase.

Example 3

RAPD Screening for Somatic Mutations

Methods

Somatic mutations in neurones were screened using genetic fingerprinting methods. DNA was obtained from the brain and the blood of all patients. PCR amplification was carried out on both samples from each patient. 10 short primers were used to randomly amplify polymorphic DNA sequences (primers listed in Table 15). PCR amplification was carried out in a final volume of 50 µl using 1.25 units of Taq DNA polymerase, 1.5 mM $MgCl_2$, 200 µM of each dNTP in PCR buffer (75 mM Tris-HCl, pH 8.8, 20 mM $(NH_4)_2SO_4$ and 0.01% Tween). The hot start (95° C. for 5 min) was followed by 40 cycles of 94° C. 30 s, AnT 1 min, 72° C. 2 min. The annealing temperature (AnT) varied between 33° C. and 39° C. depending on the primer. The PCR product was applied to a 2% agarose gel containing 1:10000 Gelstar. Electrophoresis was carried out using 1×TBE (45 mM Tris-borate/1 mM EDTA) at 6.5 V/cm for 2 hours. The RAPD sequence patterns were detected by UV light. The differences between the RAPD sequence from blood and brain DNA were compared for each patient and expressed as the % primers that led to different RAPD profiles (RAPD profiles not shown).

Results

Figure 21A:
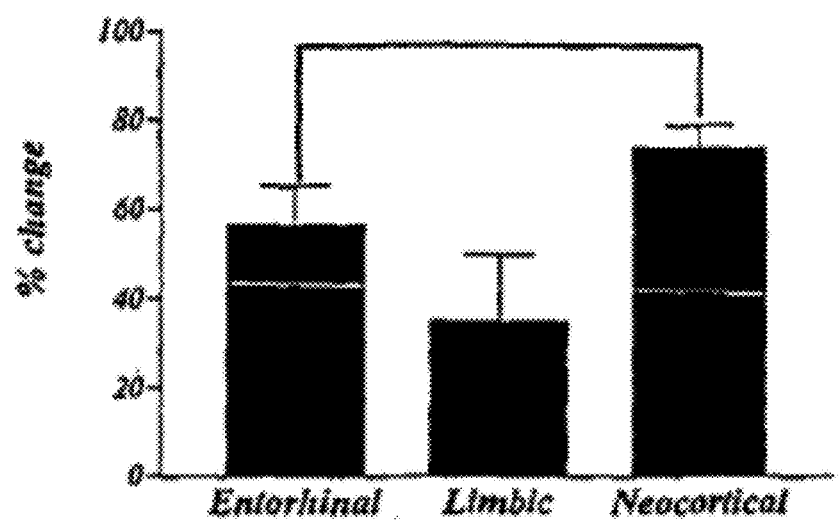
FIG. 21 illustrates the prevalence of somatic mutations in relation to AD progression and cell cycle proteins in the brain for Entorhinal, Limbic and Neocortical regions (A) and for Cyclin E negative or Cyclin E positive (B). x axis: Braak stages of AD severity; y axis: percent primers that generated differing RAPD patterns from blood when compared to brain.
Figure 21B:
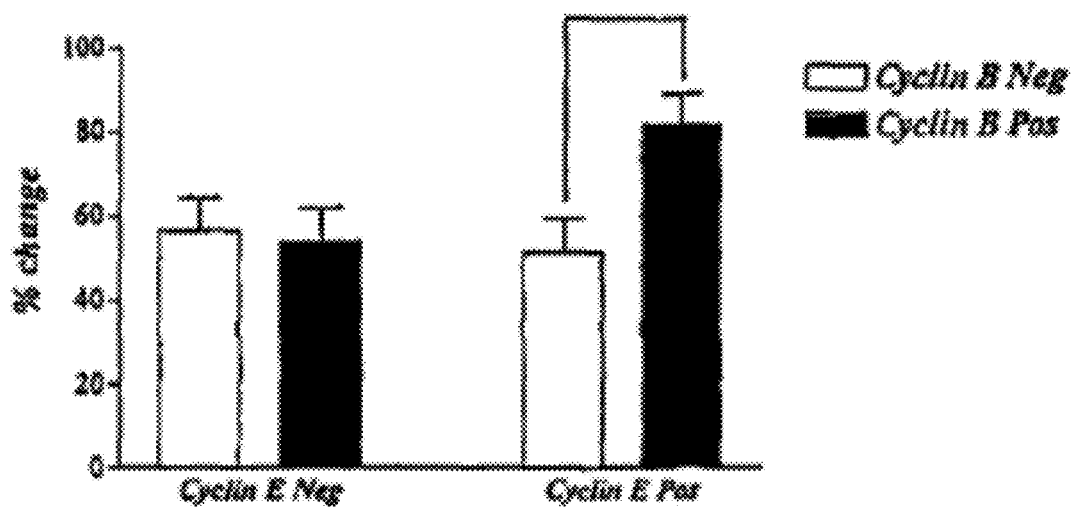

The amount of somatic mutations in the brain in AD patients was observed to be significantly associated with cell cycle deregulation and severity of AD-type pathology (FIG. 21). Therefore, it is suggested that DNA-repair insufficiency may lead to the de-regulation of the G1/S transition point finally leading to the development of Alzheimer's disease.

The genotyping findings are in concordance with previous findings in lymphocytes from AD patients that indicate that there is a detectable dysfunction at the G1/S regulation control elicited either by CDKI inducing inhibitors or by oxidative DNA damage.

TABLE 15

Primers used for RAPD analysis

| Sequence: | SEQ ID NO: |
|---|---|
| 5'-CCGGCTACGG-3' | 7 |
| 5'-CAGGCCCTTC-3' | 8 |
| 5'-TACGGACACG-3' | 9 |
| 5'-AGCTTCAGGG-3' | 10 |
| 5'-AGGCATTCCC-3' | 11 |
| 5'-GGTCTGAACC-3' | 12 |
| 5'-TAGGCTCACG-3' | 13 |
| 5'-ACGGTACACT-3' | 14 |
| 5'-GTCCTCAACG-3' | 15 |
| 5'-CAATGCGTCT-3' | 16 |

TABLE 16

OMIM Accession Numbers:

| Gene/Protein | Accession No.: |
|---|---|
| CDKN3 | 123832 |
| p15ink4B | 600431 |
| p16ink4A | 600160 |
| p19ink4D | 600927 |
| p27kip1 | 600778 |
| p21cip1 | 116899 |
| p57kip2 | 600856 |
| TP53 | 191170 |
| Gadd45A | 126335 |
| Gadd45B | 604948 |
| Gadd45G | 604949 |
| Gadd153 | 126337 |
| PCNA | 176740 |
| Ku70 | 152690 |
| KU80 | 194364 |
| Ku86 | 604611 |

TABLE 16-continued

OMIM Accession Numbers:

| Gene/Protein | Accession No.: |
|---|---|
| NDHII | 603115 |
| BLM | 604610 |
| RECQL | 600537 |
| RECQL4 | 603780 |
| RECQL5 | 603781 |

CITED REFERENCES

1. Araga S, Kagimoto H, Funamoto K and Takahashi K (1990) Jpn J Med 29: 572-5
2. Arendt T, Holzer M and Gartner U (1998) J Neural Transm 105: 949-60
3. Arendt T, Rodel L, Gartner U and Holzer M (1996) Neuroreport 7: 3047-9
4. Burke W J, McLaughlin J R. Chung H D, Gillespie K N, Grossberg G T, Luque F A and Zimmerman J (1994) Alzheimer Dis Assoc Disord 8: 22-8
5. Darzynkiewicz Z (1993) In Fantes P and Brooks R (eds) The Cell Cycle. Oxford University Press, Oxford, pp 43-68
6. Davies K J (1999) IUBMB Life 48: 41-7
7. Drabkin H A and Erickson P (1995) Prog Clin Biol Res 393: 169-76
8. Eckert A, Hartmann H, Forstl H and Muller W E (1994) Life Sci 55: 2019-29
9. Fischman H K, Reisberg B, Albu P, Ferris S H and Rainer J D (1984) Biol Psychiatry 19; 319-27
10. Fong C T and Brodeur G M (1987) Cancer Genet Cytogenet 28: 55-76
11. Mecocci P, Polidori M C, Ingegni T, Cherubini A, Chionne F. Cecchetti R and Senin U (1998) Neurology 51: 1014-1017
12. Melaragno M I. Smith Md A, Kormann Bortolotto M H and Toniolo Neto J T (1991) Gerontology 37: 293-8
13. Nagy Z, Esiri M M, Hindley N J, Joachim C, Morris J H, King E M-F, McDonald B, Litchfield S, Barnetson L, Jobst K A and Smith A D (1998) Dementia 9: 219-226
14. Nagy Z, Esiri M M and Smith A D (1998) Neuroscience 84: 731-739
15. Payao S L, Smith M D and Bertolucci P H (1998) Gerontology 44: 267-71
16. Sherr C J (1994) Stem Cells 12: 47-55; discussion 55-7
17. Tatebayashi Y, Takeda M, Kashiwagi Y, Okochi M, Kurumadani T, Sekiyama A, Kanayama G, Hariguchi S and Nishimura T (1995) Dementia 6: 9-16
18. Trieb K, Ransmayr G, Sgonc R, Lassmann H and Grubeck Loebenstein B (1996) Neurobiol Aging 17: 541-7
19. Wagner E F, Hleb M, Hanna N and Sharma S (1998) J Immunol 161: 1123-31

All Cited References and cited patents and patent publications mentioned in this specification are herein incorporated by reference to the same extent as if each individual reference, patent or publication was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method for aiding in a diagnosis of a neurological condition in a human subject, wherein said neurological condition is selected from the group consisting of:

Alzheimer's disease; incipient Alzheimer's disease; possible Alzheimer's disease;

and Alzheimer's disease associated with evidence of other type of dementia;

wherein said method comprises the steps of:

(A) determining the effectiveness of the G1/S cell cycle checkpoint exhibited by a non-neuronal and non-actively malignant cell of said subject; and (B) comparing said determined G1/S cell cycle checkpoint effectiveness with the G1/S cell cycle checkpoint effectiveness exhibited by a non-neuronal reference cell of a healthy individual or of an individual having said neurological condition to thereby determine whether a defect exists in the effectiveness of G1/S cell cycle checkpoint exhibited by said subject, wherein said defect reduces the effectiveness of G1/S checkpoint control;

whereby the presence of said defect is indicative of the neurological condition in said subject and thereby aids in the diagnosis of said neurological condition.

2. The method of claim 1 wherein said neurological condition is Alzheimer's disease.

3. The method of claim 1 wherein said step (A) is carried out by:

inducing cell division in said non-neuronal cell and testing responsiveness of said non-neuronal cell of said subject to a cell division G1 inhibitor substance, wherein reduced responsiveness to said cell division G1 inhibitor substance by said non-neuronal cell of said subject relative to that of a non-neuronal reference cell of a healthy individual indicates decreased effectiveness of the G1/S cell cycle checkpoint.

4. The method of claim 1 wherein said step (A) is carried out by:

inducing cell division in said non-neuronal cell and testing responsiveness of said non-neuronal cell of said subject to a stimulus that induces G1 cell cycle arrest, wherein a reduced responsiveness to said stimulus by said non-neuronal cell of said subject relative to that of a non-neuronal reference cell of a healthy individual indicates decreased effectiveness of the G1/S cell cycle checkpoint.

5. The method of claim 4, wherein the stimulus that induces G1 cell cycle arrest is oxidative stress, ionizing radiation, hypoxia, or UV radiation.

6. The method of claim 3 wherein the responsiveness of said non-neuronal cell of said subject to said cell division G1 inhibitor substance is determined by a cell proliferation assay, wherein higher proliferative activity in said non-neuronal cell of said subject following treatment with said cell division G1 inhibitor substance relative to that of a non-neuronal reference cell of a healthy individual indicates decreased effectiveness of the G1/S cell cycle checkpoint.

7. The method of claim 3, wherein the responsiveness of said non-neuronal cell of said subject to said cell division G1 inhibitor substance is determined by calculating the relative lengthening of the G1 phase of the cell cycle in said non-neuronal cell of said subject, wherein a reduced relative lengthening of the G1 phase following treatment with said cell division G1 inhibitor substance relative to that of a non-neuronal reference cell of a healthy individual indicates decreased effectiveness of the G1/S cell cycle checkpoint.

8. The method of claim 3 wherein the responsiveness of said non-neuronal cell of said subject to said cell division G1 inhibitor substance is determined by analysis of expression of a cell cycle regulatory protein or an mRNA encoding a cell cycle regulatory protein.

9. The method of claim 8 wherein the cell cycle regulatory protein is selected from the group consisting of CDKN3, p15ink4B, p16ink4A, p19ink4D, p27kip1, p21cip1, p57kip2 and TP53.

10. The method of claim 4 wherein the stimulus that induces G1 cell cycle arrest is DNA damage and the responsiveness of said non-neuronal cell of said subject to said stimulus is determined by analysis of expression of a DNA damage-response element.

11. The method of claim 10 wherein the DNA damage-response element is selected from the group consisting of TP53, Gadd34, Gadd45A, Gadd45B, Gadd45G, Gadd153 and PCNA.

12. The method of claim 3 wherein the responsiveness of said non-neuronal cell of said subject to said cell division G1 inhibitor substance is determined by assessment of cell viability or cell death, wherein increased cell survival or a reduced degree of cell death in said non-neuronal cell of said subject following treatment with said cell division G1 inhibitor substance relative to that of a non-neuronal reference cell of a healthy individual indicates decreased effectiveness of the G1/S cell cycle checkpoint.

13. The method of claim 3 wherein the responsiveness of said non-neuronal cell of said subject to said cell division G1 inhibitor substance is determined by analysis of expression of a cell death related protein or an mRNA encoding a cell death related protein.

14. The method of claim 13 wherein the cell death related protein is a member of the bcl-2 family of proteins.

15. The method of claim 3 wherein the responsiveness of said non-neuronal cell of said subject to said cell division G1 inhibitor substance is determined by assessment of DNA content of said non-neuronal cell of said subject with or without cell cycle analysis.

16. The method of claim 1, wherein said non-neuronal cell of said subject is a lymphocyte.

17. The method of claim 4, wherein the responsiveness of said non-neuronal cell of said subject to said stimulus that induces G1 cell cycle arrest is determined by a cell proliferation assay, wherein higher proliferative activity in said non-neuronal cell of said subject following exposure to said stimulus that induces G1 cell cycle arrest relative to that of a non-neuronal reference cell of a healthy individual indicates decreased effectiveness of the G1/S cell cycle checkpoint.

18. The method of claim 4, wherein the responsiveness of said non-neuronal cell of said subject to said stimulus that induces G1 cell cycle arrest is determined by calculating the relative lengthening of the G1 phase of the cell cycle in said non-neuronal cell of said subject, wherein a reduced relative lengthening of the G1 phase following exposure to said stimulus that induces G1 cell cycle arrest relative to that of a non-neuronal reference cell of a healthy individual indicates decreased effectiveness of the G1/S cell cycle checkpoint.

19. The method of claim 4 wherein the responsiveness of said non-neuronal cell of said subject to said stimulus that induces G1 cell cycle arrest is determined by analysis of expression of a cell cycle regulatory protein or an mRNA encoding a cell cycle regulatory protein.

20. The method of claim 19 wherein the cell cycle regulatory protein is selected from the group consisting of CDKN3, p15ink4B, p16ink4A, p19ink4D, p27kip1, p21cip1, p57kip2 and TP53.

21. The method of claim 4 wherein the responsiveness of said non-neuronal cell of said subject to said stimulus that induces G1 cell cycle arrest is determined by assessment of cell viability or cell death, wherein increased cell survival or a reduced degree of cell death in said non-neuronal cell of said subject following exposure to said stimulus that induces G1 cell cycle arrest relative to that of a non-neuronal reference cell of a healthy individual indicates decreased effectiveness of the G1/S cell cycle checkpoint.

22. The method of claim 4 wherein the responsiveness of said non-neuronal cell of said subject to said stimulus which induces G1 cell cycle arrest is determined by analysis of expression of a cell death related protein or an mRNA encoding a cell death related protein.

23. The method of claim 22 wherein the cell death related protein is a member of the bcl-2 family of proteins.

24. The method of claim 4 wherein the responsiveness of said non-neuronal cell of said subject to said stimulus which induces G1 cell cycle arrest is determined by assessment of DNA content of said non-neuronal cell of said subject with or without cell cycle analysis.

* * * * *

SEQUENCE LISTING

<160> NUMBER OF SEQ ID NOS: 16

<210> SEQ ID NO 1
<211> LENGTH: 28
<212> TYPE: DNA
<213> ORGANISM: Homo sapiens

<400> SEQUENCE: 1
cgggatccgg cgccatgtca gaaccggc                                              28

<210> SEQ ID NO 2
<211> LENGTH: 20
<212> TYPE: DNA
<213> ORGANISM: Homo sapiens

<400> SEQUENCE: 2
ccagacaggt cagcccttgg                                                       20

<210> SEQ ID NO 3
<211> LENGTH: 18
<212> TYPE: DNA
<213> ORGANISM: Homo sapiens

<400> SEQUENCE: 3
ggccatgtcc gacgcgtc                                                         18

<210> SEQ ID NO 4
<211> LENGTH: 20
<212> TYPE: DNA
<213> ORGANISM: Homo sapiens

<400> SEQUENCE: 4
aggcggcagc gccccacctg                                                       20

<210> SEQ ID NO 5
<211> LENGTH: 23
<212> TYPE: DNA
<213> ORGANISM: Homo sapiens

<400> SEQUENCE: 5
attacgactt ccagcaggac atg                                                   23

<210> SEQ ID NO 6
<211> LENGTH: 21
<212> TYPE: DNA
<213> ORGANISM: Homo sapiens

<400> SEQUENCE: 6
ctggagccag gaccgggact g                                                     21

<210> SEQ ID NO 7
<211> LENGTH: 10
<212> TYPE: DNA
<213> ORGANISM: Homo sapiens

<400> SEQUENCE: 7
ccggctacgg                                                                  10

<210> SEQ ID NO 8
<211> LENGTH: 10
<212> TYPE: DNA
<213> ORGANISM: Homo sapiens

```
<400> SEQUENCE: 8
caggcccttc                                                            10

<210> SEQ ID NO 9
<211> LENGTH: 10
<212> TYPE: DNA
<213> ORGANISM: Homo sapiens

<400> SEQUENCE: 9
tacggacacg                                                            10

<210> SEQ ID NO 10
<211> LENGTH: 10
<212> TYPE: DNA
<213> ORGANISM: Homo sapiens

<400> SEQUENCE: 10
agcttcaggg                                                            10

<210> SEQ ID NO 11
<211> LENGTH: 10
<212> TYPE: DNA
<213> ORGANISM: Homo sapiens

<400> SEQUENCE: 11
aggcattccc                                                            10

<210> SEQ ID NO 12
<211> LENGTH: 10
<212> TYPE: DNA
<213> ORGANISM: Homo sapiens

<400> SEQUENCE: 12
ggtctgaacc                                                            10

<210> SEQ ID NO 13
<211> LENGTH: 10
<212> TYPE: DNA
<213> ORGANISM: Homo sapiens

<400> SEQUENCE: 13
taggctcacg                                                            10

<210> SEQ ID NO 14
<211> LENGTH: 10
<212> TYPE: DNA
<213> ORGANISM: Homo sapiens

<400> SEQUENCE: 14
acggtacact                                                            10

<210> SEQ ID NO 15
<211> LENGTH: 10
<212> TYPE: DNA
<213> ORGANISM: Homo sapiens

<400> SEQUENCE: 15
gtcctcaacg                                                            10

<210> SEQ ID NO 16
<211> LENGTH: 10
<212> TYPE: DNA
<213> ORGANISM: Homo sapiens
```

```
<400> SEQUENCE: 16
caatgcgtct                                                                    10
```